(12) United States Patent
Alberti et al.

(10) Patent No.: US 8,507,664 B2
(45) Date of Patent: Aug. 13, 2013

(54) **OLIGONUCLEOTIDIC SEQUENCES ABLE TO SILENCE THE EXPRESSION OF THE *CYCLIN D1-TROP2* CHIMERA AND USES THEREOF IN MEDICAL FIELD**

(75) Inventors: Saverio Alberti, Chieti Scalo Ch (IT); Emanuela Guerra, Chieti Scalo Ch (IT)

(73) Assignee: Saverio Alberti, Chieti Scalo CH (IT)

( * ) Notice: Subject to any disclaimer, the term of this patent is extended or adjusted under 35 U.S.C. 154(b) by 0 days.

(21) Appl. No.: 13/121,137

(22) PCT Filed: Sep. 25, 2009

(86) PCT No.: PCT/IT2009/000437
§ 371 (c)(1),
(2), (4) Date: May 13, 2011

(87) PCT Pub. No.: WO2010/035304
PCT Pub. Date: Apr. 1, 2010

(65) Prior Publication Data
US 2011/0213015 A1    Sep. 1, 2011

(30) Foreign Application Priority Data
Sep. 25, 2008    (IT) .............................. CH2008A0021

(51) Int. Cl.
*C07H 21/00* (2006.01)
(52) U.S. Cl.
USPC ......... 536/24.5; 536/34.31; 536/24.1; 514/44
(58) Field of Classification Search
None
See application file for complete search history.

(56) References Cited

PUBLICATIONS

Wang et al. (Mol Cancer Ther Feb. 15, 2008, 7:280-285).*
Terrinoni et al. (Genes, Chromosomes & Cancer 31:209-220, 2001).*
Scherr et al. (Blood 2003, 101:1566-1569).*
PubMed Genbank Accession X77754.*
Pirollo et al. (Cancer Res 2008, 68:1247-1250).*
Guerra et al. Cancer Res 2008: 68:(19), 8113-8121.*
PubMed Genbank Accession X77754 Oct. 2008.*

\* cited by examiner

*Primary Examiner* — Kimberly Chong
(74) *Attorney, Agent, or Firm* — Arent Fox LLP

(57) ABSTRACT

The invention concerns RNA oligonucleotide sequences or sequences that are transcribed into RNA or analogous molecules able to silence the expression of the CYCLIN D1/TROP2 chimeric mRNA and their use in the treatment and the prevention of tumors.

12 Claims, 11 Drawing Sheets

Figure 4:
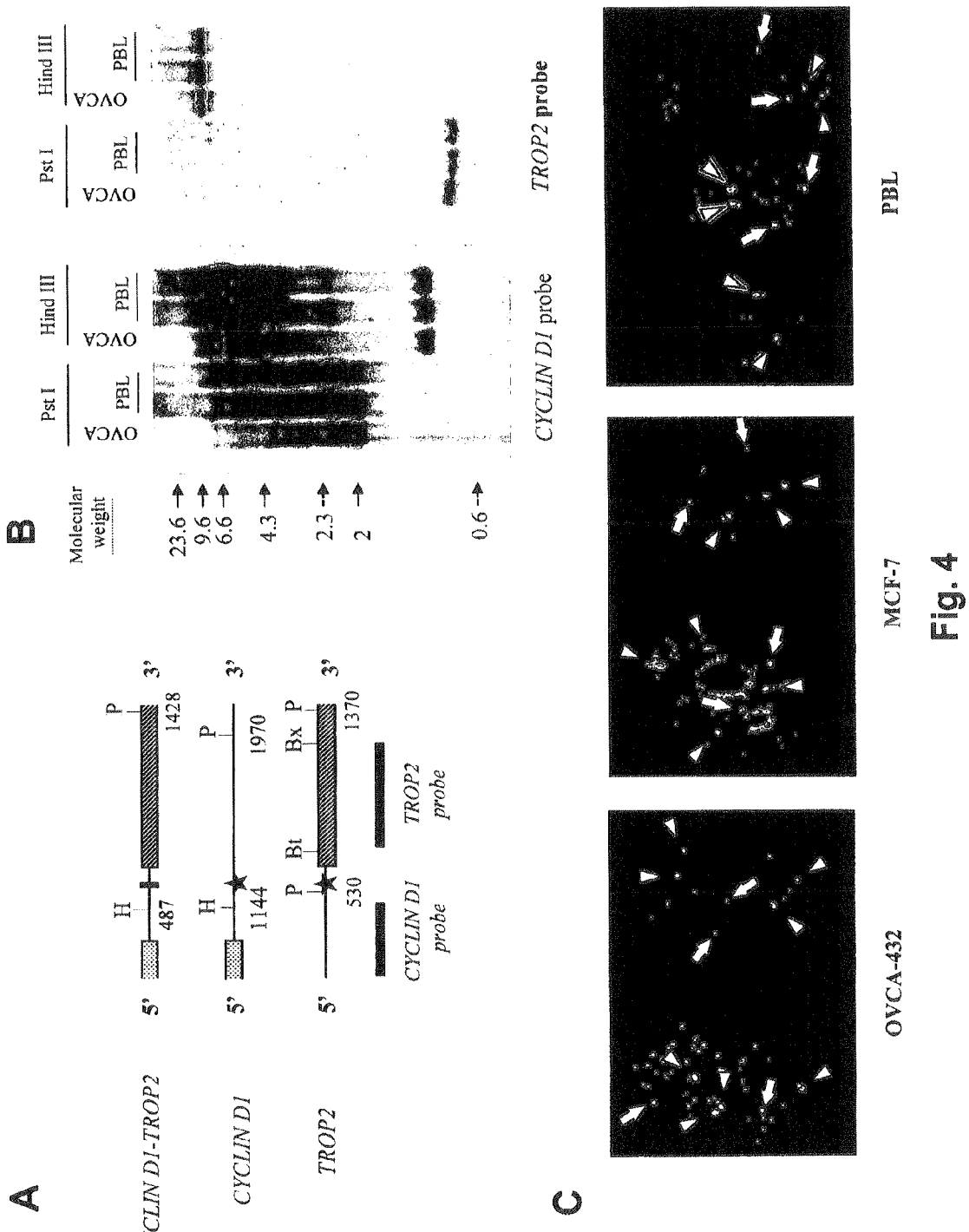

**Sequence of the *CYCLIN D1-TROP2* chimeric mRNA (SEQ ID NO : 18)**

```
GCAGUAGCAGCGAGCAGCAGAGUCCGCACGCUCCGGCGAGGGGCAGAAGAGCGCGAGGGAGCGCGGGGCA
GCAGAAGCGAGAGCCGAGCGCGGACCCAGCCAGGACCCACAGCCCUCCCCAGCUGCCCAGGAAGAGCCCC
AGCCAUGGAACACCAGCUCCUGUGCUGCGAAGUGGAAACCAUCCGCCGCGCGUACCCCGAUGCCAACCUC
CUCAACGACCGGGUGCUGCGGGCCAUGCUGAAGGCGGAGGAGACCUGCGCGCCCUCGGUGUCCUACUUCA
AAUGUGUGCAGAAGGAGGUCCUGCCGUCCAUGCUGAAGAUCGUCGCCACCUGGAUGCUGGAGGUCUGCGA
GGAACAGAAGUGCGAGGAGGAGGUCUUCCCGCUGGCCAUGAACUACCUGGACCGCUUCCUGUCGCUGGAG
CCCGUGAAAAAGAGCCGCCUGCAGCUGCUGGGGGCCACUUGCAUGUUCGUGGCCUCUAAGAUGAAGGAGA
CCAUCCCCCUGACGGCCGAGAAGCUGUGCAUCUACACCGACGGCUCCAUCCGGCCCGAGGAGCUGCUGCA
AAUGGAGCUGCUCCUGGUGAACAAGCUCAAGUGGAACCUGGCCGCAAUGACCCCGCACGAUUUCAUUGAA
CACUUCCUCUCCAAAAUGCCAGAGGCGGAGGAGAACAAACAGAUCAUCCGCAAACACGCGCAGACCUUCG
UUGCCUCUUGUGCCACAGAUGUGAAGUUCAUUUCCAAUCCGCCCUCCAUGGUGGCAGCGGGGAGCGUGGU
GGCCGCAGUGCAAGGCCUGAACCUGAGGAGCCCCAACAACUUCCUGUCCUACUACCGCCUCACACGCUUC
CUCUCCAGAGUGAUCAAGUGUGACCCAGACUGCCUCCGGGCCUGCCAGGAGCAGAUCGAAGCCCUGCUGG
AGUCAAGCCUGCGCCAGGCCCAGCAGAACAUGGACCCCAAGGCCGCCGAGGAGGAGGAAGAGGAGGAGGA
GGAGGUGGACCUGGCUUGCACACCCACCGACGUGCGGGACGUGGACAUCUGAGGGGCCCAGGCAGGCGGG
CGCCACCGCCACCCGCAGCGAGGCGGAGCCGGCCCCAGGUGCUCCACAUGACAGUCCCUCCUCUCCGGA
GCAUUUUGAUACCAGAAGGGAAAGCUUCAUUCUCCUUGUUGUUGGUUGUUUUUCCUUUGCUCUUUCCCC
CUUCCAUCUCUGACUUAAGCAAAAGAAAAAGAUUACCCAAAAACUGUCUUUAAAAGAGAGAGAGAGAAA
GGAGCCCGAGCCCCGACGAGUCCCCGCGCCUCAUCCGCCCGCGUCCGGUCCGCGUUCCUCCGCCCCACCA
UGGCUCGGGCCCCGGCCUCGCGCCGCCACCGCUGCGGCUGCCGCUGCUGCUGGUGCUGGCGGCGGU
GACCGGCCACACGGCCGCGCAGGACAACUGCACGUGUCCCACCAACAAGAUGACCGUGUGCAGCCCCGAC
GGCCCCGGCGGCCGCUGCCAGUGCCGCGCGCUGGGCUCGGGCAUGGCGGUCGACUGCUCCACGCUGACCU
CCAAGUGUCUGCUGCUCAAGGCGCGCAUGAGCGCCCCCAAGAACGCCCGCACGCUGGUGCGGCCGAGUGA
GCACGCGCUCGUGGACAACGAUGGCCUCUACGACCCCGACUGCGACCCCGAGGGCCGCUUCAAGGCGCGC
CAGUGCAACCAGACGUCGGUGUGCUGGUGCGUGAACUCGGUGGGCGUGCGCCGCACGGACAAGGGCGACC
UGAGCCUACGCUGCGAUGAGCUGGUGCGCACCCACCACAUCCUCAUUGACCUGCGCCACCGCCCCACCGC
CGGCGCCUUCAACCACUCAGACCUGGACGCCGAGCUGAGGCGGCUCUUCCGCGAGCGCUAUCGGCUGCAC
CCCAAGUUCGUGGCGGCCGUGCACUACGAGCAGCCCACCAUCCAGAUCGAGCUGCGGCAGAACACGUCUC
AGAAGGCCGCCGGUGAAGUGGAUAUCGGCGAUGCCGCCUACUACUUCGAGAGGGACAUCAAGGGCGAGUC
UCUAUUCCAGGGCCGCGGCGGCCUGGACUUGCGCGUGCGCGGAGAACCCUGCAGGUGGAGCGCACGCUC
AUCUAUUACCUGGACGAGAUUCCCCGAAGUUCUCCAUGAAGCGCCUCACCGCCGGCCUCAUCGCCGUCA
UCGUGGUGGUCGUGGUGGCCCUCGUCGCCGGCAUGGCCGUCCUGGUGAUCACCAACCGGAGAAAGUCGGG
GAAGUACAAGAAGGUGGAGAUCAAGGAACUGGGGGAGUUGAGAAAGGAACCGAGCUUGUAGGUACCCGGC
GGGGCAGGGGAUGGGGUGGGGUACCGGAUUUCGGUAUCGUCCCAGACCCAAGUGAGUCACGCUUCCUGAU
UCCUCGGCGCAAAGGAGACGUUUAUCCUUUCAAAUUCCUGCCUUCCCCCUCCCUUUUGCGCACACACCAG
GUUUAAUAGAUCCUGGCCUCAGGGUCUCCUUUCUUUCUCACUUCUGUCUUGAGGGAAGCAUUUCUAAAAU
GUAUCCCCUUUCGGUCCAACAACAGGAAACCUGACUGGGGCAGUGAAGGAAGGGAUGGCACAGCGUUAUG
UGUAAAAAACAAGUAUCUGUAUGACAACCCGGACGUUUGCAAGUAACUGAAUCCAUUGCGACAUUGUG
AAGGCUUAAAUGAGUUUAGAUGGGAAAUAGCGUUGUUAUCGCCUUGGGUUUAAAUUAUUUGAUGAGUUCC
ACUUGUAUCAUGGCCUACCCGAGGAGAAGAGGAGUUUGUUAACGGGCCUAUGUAGUAGCCUCAUUUACC
AUCGUUUGUAUUACUGACCACAUAUGCUUGUCACUGGGAAAGAAGCCUGUUUCAGCUGCCUGAACGCAGU
UUGGAUGUCUUUGAGGACAGACAUUGCCCGGAAACUCAGUCUAUUUAUUCUUCAGCUUGCCCUUACUGCC
ACUGAUAUUGGUAAUGUUCUUUUUUGUAAAAUGUUUGUACAUAUGUUGUCUUUGAUAAUGUUGCUGUAAU
UUUUUAAAAUAAAACACGAAUUUAAUAAAAUAUGGGAAAGGCACAAACCAGAAGUCGGCAUUUGUGAAAA
GUCCCUCCAGAUUUCUAUCACUUUGGUCUCUAAUUUCCCAAGACUUGUAUUUUUUUUAUUUCAAAUUA
UAACACUUUUUUUUCCCCCAGAAGUGGGUGUUUCAUGUUGCUACUCUGGUGUGUCCCAAGAUAUCCUAAC
UGGCCAGUGUAAAUGCUAUUCUUUCUAAAUAAGAUUAUUUGGAAAUUCCUUCAAACUGCAGGAGGGCGA
GCUCUGAGGGCACGAGAAGCUAAAACUAGCUGCUUUUGAUGAAAAAGAGUGCCAGUCUUUGGUCAUCUCU
AAACAAGGCUUAUCACCAAUGGAGACAGAAAACUCUAGUUCAAGAGCUGUACCUCCUUUGAAUCCCAGCC
CUACUCGAAAUAAGUGGUACUAUUUCCAUUUAGCCUUUGAGCAAAUCACUUAACUCAAAGGCGUUGUGGC
UCUAAGAUUAAACGACUUU
```

Fig. 1A

Primers used to detect the the *CYCLIN D1-TROP2* chimeric mRNA by means of quantitative PCR

| | | |
|---|---|---|
| PRAD1.F3 (forward) | 5' CTGGCCGCAATGACCCCGCA 3' | (SEQ ID NO : 4) |
| T2.F5c (reverse) | 5' GGCGGAGGAACGCGGACCGG 3' | (SEQ ID NO : 9) |
| PRAD1.F4 (forward) | 5' GCGGGATCCAAGGGAAAGCTTCATTCT 3' | (SEQ ID NO : 5) |
| T2.F5tris (reverse) | 5' GAGGCGCGGGGACTCGTCGG 3' | (SEQ ID NO : 10) |
| PRAD1.F5 (forward) | 5' GCGGGATCCCCTTGTTGTT GGTTGTTT 3' | (SEQ ID NO : 6) |

Fig. 1B

Sequences of the siRNAs able to silence the expression of the *CYCLIN D1-TROP2* chimera (siRNA-CH) and of the mismatched, ineffective siRNAs (siRNA-MM) as negative controls siRNA-CH, forward (SEQ ID NO : 1)
5' GATCCCCGAGAGAGAGAGAAAGGAGCCCTTCAAGAGAGGGCTCCTTTCTCTCTCTCTCTTTTTGGA AA 3' siRNA-CH, reverse (SEQ ID NO : 2)
5' AGCTTTTCCAAAAAGAGAGAGAGAGAAAGGAGCCCTCTCTTGAAGGGCTCCTTTCTCTCTCTCTCG GG 3' siRNA-MM, forward; the two mismatched nucleotides with respect to the chimera sequence are underlined: (SEQ ID NO : 19)
5' GATCCCCGAGA_TAGAGAGAAAG_TAGCCCTTCAAGAGAGGGCTACTTTCTCTCTATCTCTTTTTGGA AA 3' siRNA-MM, reverse (SEQ ID NO : 20)
5' AGCTTTTCCAAAAAGAGATAGAGAGAAAGTAGCCCTCTCTTGAAGGGCTACTTTCTCTCTATCTCG GG 3'

Fig. 1C

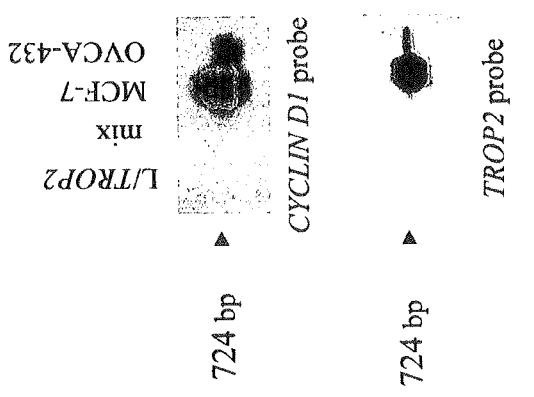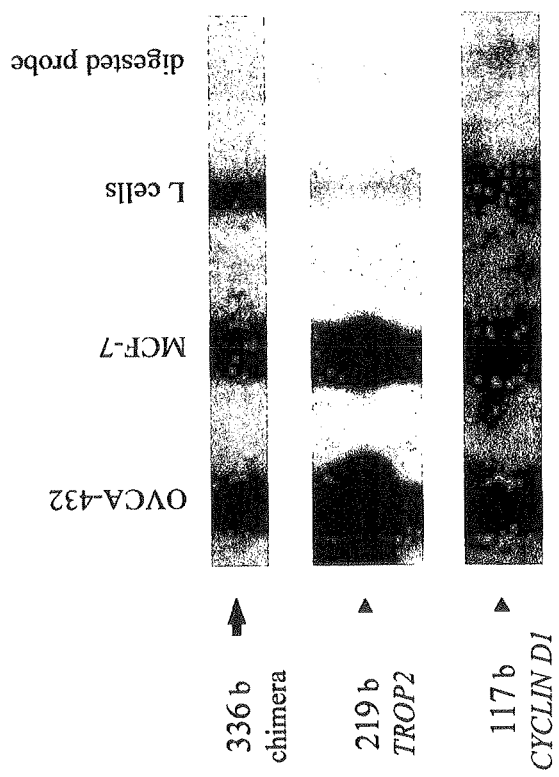
Fig. 2

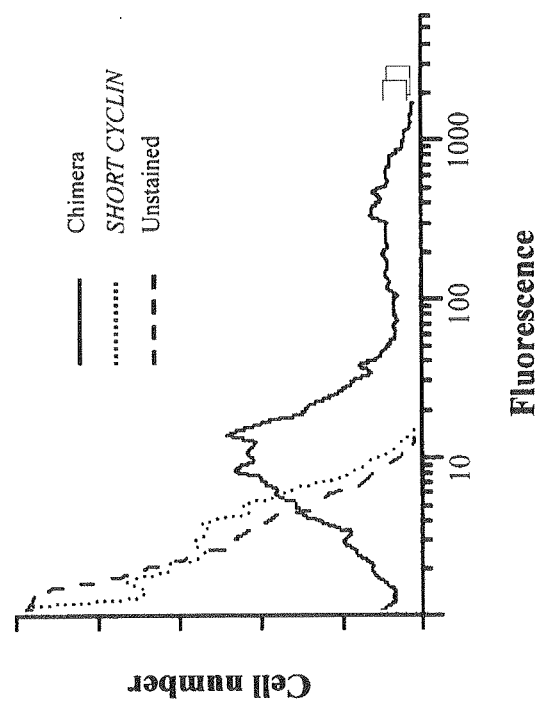
Fig. 3

```
                         SEQUENCE LISTING

<160> NUMBER OF SEQ ID NOS: 21

<210> SEQ ID NO 1
<211> LENGTH: 68
<212> TYPE: DNA
<213> ORGANISM: artificial
<220> FEATURE:
<223> OTHER INFORMATION: siRNA amplification forward primer

<400> SEQUENCE: 1
gatccccgag agagagagaa aggagccctt caagagaggg ctcctttctc tctctctctt    60
tttggaaa                                                             68

<210> SEQ ID NO 2
<211> LENGTH: 68
<212> TYPE: DNA
<213> ORGANISM: artificial
<220> FEATURE:
<223> OTHER INFORMATION: siRNA amplification reverse primer

<400> SEQUENCE: 2
agcttttcca aaaagagaga gagagaaagg agccctctct tgaagggctc ctttctctct    60
ctctcggg                                                             68

<210> SEQ ID NO 3
<211> LENGTH: 20
<212> TYPE: DNA
<213> ORGANISM: artificial
<220> FEATURE:
<223> OTHER INFORMATION: amplification forward primer complementary to
      cyclin D1

<400> SEQUENCE: 3
cccagctgcc caggaagagc                                                20

<210> SEQ ID NO 4
<211> LENGTH: 20
<212> TYPE: DNA
<213> ORGANISM: artificial
<220> FEATURE:
<223> OTHER INFORMATION: amplification forward primer complementary to
      cyclin D1

<400> SEQUENCE: 4
ctggccgcaa tgacccccgca                                               20

<210> SEQ ID NO 5
```

-continued

```
<211> LENGTH: 27
<212> TYPE: DNA
<213> ORGANISM: artificial
<220> FEATURE:
<223> OTHER INFORMATION: amplification forward primer complementary to
      cyclin D1

<400> SEQUENCE: 5
gcgggatcca agggaaagct tcattct                                            27

<210> SEQ ID NO 6
<211> LENGTH: 27
<212> TYPE: DNA
<213> ORGANISM: artificial
<220> FEATURE:
<223> OTHER INFORMATION: amplification forward primer complementary to
      cyclin D1

<400> SEQUENCE: 6
gcgggatccc cttgttgttg gttgttt                                            27

<210> SEQ ID NO 7
<211> LENGTH: 20
<212> TYPE: DNA
<213> ORGANISM: artificial
<220> FEATURE:
<223> OTHER INFORMATION: amplification reverse primer complementary to
      TROP2

<400> SEQUENCE: 7
atcgttgtcc acgagcgcgt                                                    20

<210> SEQ ID NO 8
<211> LENGTH: 20
<212> TYPE: DNA
<213> ORGANISM: artificial
<220> FEATURE:
<223> OTHER INFORMATION: amplification reverse primer complementary to
      TROP2

<400> SEQUENCE: 8
ttggtgggac acgtgcagtt                                                    20

<210> SEQ ID NO 9
<211> LENGTH: 20
<212> TYPE: DNA
<213> ORGANISM: artificial
<220> FEATURE:
<223> OTHER INFORMATION: amplification reverse primer complementary to
      TROP2

<400> SEQUENCE: 9
ggcggaggaa cgcggaccgg                                                    20

<210> SEQ ID NO 10
<211> LENGTH: 20
<212> TYPE: DNA
<213> ORGANISM: artificial
<220> FEATURE:
<223> OTHER INFORMATION: amplification reverse primer complementary to
      TROP2

<400> SEQUENCE: 10
gaggcgcggg gactcgtcgg                                                    20

<210> SEQ ID NO 11
<211> LENGTH: 23
<212> TYPE: DNA
```

```
<213> ORGANISM: artificial
<220> FEATURE:
<223> OTHER INFORMATION: amplification forward primer for the detection
      of cyclin D1 mRNA

<400> SEQUENCE: 11
acaaacagat catccgcaaa cac                                              23

<210> SEQ ID NO 12
<211> LENGTH: 20
<212> TYPE: DNA
<213> ORGANISM: artificial
<220> FEATURE:
<223> OTHER INFORMATION: amplification reverse primer for the detection
      of cyclin D1 mRNA

<400> SEQUENCE: 12
tgttggggct cctcaggttc                                                  20

<210> SEQ ID NO 13
<211> LENGTH: 20
<212> TYPE: DNA
<213> ORGANISM: artificial
<220> FEATURE:
<223> OTHER INFORMATION: amplification forward primer for the detection
      of TROP2 mRNA

<400> SEQUENCE: 13
gcaggacaac tgcacgtgtc                                                  20

<210> SEQ ID NO 14
<211> LENGTH: 19
<212> TYPE: DNA
<213> ORGANISM: artificial
<220> FEATURE:
<223> OTHER INFORMATION: amplification forward primer for 28S ribosome
      RNA

<400> SEQUENCE: 14
ttgaaaatcc gggggagag                                                   19

<210> SEQ ID NO 15
<211> LENGTH: 20
<212> TYPE: DNA
<213> ORGANISM: artificial
<220> FEATURE:
<223> OTHER INFORMATION: amplification reverse primer for 28S ribosome
      RNA

<400> SEQUENCE: 15
acattgttcc aacatgccag                                                  20

<210> SEQ ID NO 16
<211> LENGTH: 20
<212> TYPE: DNA
<213> ORGANISM: artificial
<220> FEATURE:
<223> OTHER INFORMATION: amplification forward primer for the chimera
      junction sequence

<400> SEQUENCE: 16
gactgcctcc gggcctgcca                                                  20

<210> SEQ ID NO 17
<211> LENGTH: 20
<212> TYPE: DNA
<213> ORGANISM: artificial
<220> FEATURE:
```

<223> OTHER INFORMATION: amplification forward primer for the chimera
      junction sequence

<400> SEQUENCE: 17
tcctttgctc tttcccctt                                                    20

<210> SEQ ID NO 18
<211> LENGTH: 3518
<212> TYPE: RNA
<213> ORGANISM: artificial
<220> FEATURE:
<223> OTHER INFORMATION: sequence of the CYCLIN D1-TROP2 chimeric mRNA

<400> SEQUENCE: 18
gcaguagcag cgagcagcag aguccgcacg cuccggcgag gggcagaaga gcgcgaggga      60
gcgcggggca gcagaagcga gagccgagcg cggacccagc caggacccac agcccucccc     120
agcugcccag gaagagcccc agccauggaa caccagcucc ugugcugcga aguggaaacc     180
auccgccgcg cguaccccga ugccaaccuc ucaacgacc gggugcugcg ggccaugcug      240
aaggcggagg agaccugcgc gcccucggug uccuacuuca aaugugugca gaaggagguc     300
cugccgucca ugcggaagau cgucgccacc uggaugcugg aggucgcga ggaacagaag      360
ugcgaggagg aggucuuccc gcuggccaug aacuaccugg accgcuuccu gucgcuggag     420
cccgugaaaa agagccgccu gcagcugcug ggggccacuu gcauguucgu ggccucuaag     480
augaaggaga ccauccccu gacggccgag aagcugugca ucuacaccga cggcuccauc      540
cggcccgagg agcugcugca aauggagcug uccugguga caagcucaa guggaaccug       600
gccgcaauga ccccgcacga uuucauugaa cauuccucu ccaaaaugcc agaggcggag      660
gagaacaaac agaucauccg caaacacgcg cagaccuucg uugccucuug ugccacagau     720
gugaaguuca uuccaauccc gccuccaug guggcagcgg ggagcguggu ggccgcagug      780
caaggccuga accugaggag ccccaacaac uuccugccu acuaccgccu cacacgcuuc     840
cucuccagag ugaucaagug ugacccagac ugccuccggg ccugccagga gcagaucgaa     900
gcccugcugg agucaagccu cgcgcaggcc cagcagaaca uggaccccaa ggccgccgag     960
gaggaggaag aggaggagga ggagguggac cuggcuugca cccaccgacg ugcgggac       1020
guggacaucu gaggggccca ggcaggcggg cgccaccgcc acccgcagcg agggcggagc     1080
cggccccagg ugcuccacau gacagucccu ccucuccgga gcauuuugau accagaaggg     1140
aaagcuucau ucuccuuguu guugguuguu uuuccuuug cucuuuccc cuuccaucuc      1200
ugacuuaagc aaaagaaaaa gauuacccaa aaacugucuu uaaagagag agagagaaag     1260
gagcccgagc cccgacgagu ccccgcgccu cauccgcccg cguccggucc gcguuccucc     1320
gccccaccau ggcucggggc cccggccucg cgccgccacc gcugcggcug ccgcugcugc     1380
ugcuggugcu ggcggcggug accgccaca cggccgcgca ggacaacugc acgguccca     1440
ccaacaagau gaccgugugc agcccgacg gccccggcgg ccgcugccag ugccgcgcgc     1500
ugggcucggg cauggcgguc gacugcucca cgcugaccuc caaguucug cugcucaagg     1560
cgcgcaugag cgccccaag aacgcccgca cgcuggugcg gccgagugag cacgcgcucg     1620
uggacaacga uggccucuac gaccccgacu gcgaccccga gggccgcuuc aaggcgcgcc     1680
agugcaacca gacgucgguu gcuggugcg ugaacucggu gggcgugcgc cgcacggaca     1740
agggcgaccu gagccuacgc ugcgaugagc uggugcgcac ccaccacauc cucauugacc     1800
ugcgccaccg cccaccgcc ggcgccuuca ccaccacaga ccuggacgcc gagcugaggc     1860
ggcucuuccg cgagcgcuau cggcugcacc ccaaguucgu ggcggccgug cacacgagc     1920

```
agcccaccau ccagaucgag cugcggcaga acacgucuca gaaggccgcc ggugaagugg      1980
auaucggcga ugccgccuac uacuucgaga gggacaucaa gggcgagucu cuauuccagg      2040
gccgcggcgg ccuggacuug cgcgugcgcg gagaaccccu gcagguggag cgcacgcuca      2100
ucuauuaccu ggacgagauu cccccgaagu ucuccaugaa gcgccucacc gccggccuca      2160
ucgccgucau cguggugguc gugguggccc ucgucgccgg cauggccguc cuggugauca      2220
ccaaccggag aaagucgggg aaguacaaga agguggagau caaggaacug ggggaguuga      2280
gaaaggaacc gagcuuguag guacccggcg gggcagggga uggggugggg uaccggauuu      2340
cgguaucguc ccagacccaa gugagucacg cuuccugauu ccucggcgca aaggagacgu      2400
uuauccuuuc aaauuccugc cuuccccuc ccuuuugcgc acacaccagg uuuaauagau       2460
ccuggccuca gggucuccuu ucuuucucac uucugucuu agggaagcau ucuaaaaug       2520 uaucccuuu cgguccaaca acaggaaacc ugacuggggc agugaaggaa gggauggcac       2580
agcguuaugu guaaaaaaca aguaucugua ugacaacccg ggaucguuug caaguaacug      2640
aauccauugc gacauuguga aggcuuaaau gaguuuagau gggaaauagc guuguuaucg      2700
ccuuggguuu aaauuauuug augaguucca cuuguaucaa ggccuacccg aggagaagag      2760
gaguuuguua acugggccua uguaguagcc ucauuuacca ucguuuguau uacugaccac      2820
auaugcuugu cacuggaaaa gaagccuguu ucagcgccu gaacgcaguu uggaugucuu       2880
ugaggacaga cauugcccgg aaacucaguc uauuuauucu ucagcuugcc cuuacugcca      2940
cugauauugg uaauguucuu uuuuguaaaa uguuugacu auguuugucu uugauaaugu       3000
ugcuguaauu uuuuaaaaua aaacacgaau uuaauaaaau augggaaagg cacaaaccag      3060
aagucggcau uugugaaaag ucccuccaga uuucuaucac uuuggucucu aauuucccaa      3120
gacuuguauu uuuuuuuau uucaaauuau aacacuuuuu uucccccag aaguggguguu       3180 uucauguugc uacucuggug uguccaagaa uauccuaacu ggccagugua aaugcuauuc      3240
uuucuaaaua agauuauuug gaaacuuccu ucaaacugca ggagggcgag cucugagggc      3300
acgagaagcu aaaacuagcu gcuuuugaug aaaagagug ccagucuuug gucaucucua      3360
aacaaggcuu aucaccaaug gagacagaaa acucaguuc aagagcugua ccuccuuuga      3420
aucccagccc uacucgaaau aaguggauacu auuccauuu agccuuugag caaaucacuu      3480
aacucaaagg cguuguggcu cuaagauuaa acgacuuu                            3518
```

<210> SEQ ID NO 19
<211> LENGTH: 68
<212> TYPE: DNA
<213> ORGANISM: artificial
<220> FEATURE:
<223> OTHER INFORMATION: siRNA amplification forward primer

<400> SEQUENCE: 19

```
gatccccgag atagagagaa agtagccctt caagagaggg ctactttctc tctatctctt      60
tttggaaa                                                              68
```

<210> SEQ ID NO 20
<211> LENGTH: 68
<212> TYPE: DNA
<213> ORGANISM: artificial
<220> FEATURE:
<223> OTHER INFORMATION: siRNA amplification reverse primer

<400> SEQUENCE: 20

```
agcttttcca aaaagagata gagagaaagt agccctctct tgaagggcta ctttctctct      60
```

```
atctcggg                                                              68

<210> SEQ ID NO 21
<211> LENGTH: 21
<212> TYPE: RNA
<213> ORGANISM: artificial
<220> FEATURE:
<223> OTHER INFORMATION: cyclin D1-TROP2 junction sequence

<400> SEQUENCE: 21
gagagagaga gaaaggagcc c                                               21
```

OLIGONUCLEOTIDIC SEQUENCES ABLE TO SILENCE THE EXPRESSION OF THE CYCLIN D1-TROP2 CHIMERA AND USES THEREOF IN MEDICAL FIELD

CROSS-REFERENCE TO RELATED APPLICATION

This application is a National Stage entry of International Application No. PCT/IT2009/000437, having an international filing date of Sep. 25, 2009, which claims priority to Italian Application No.: CH2008A000021, filed Sep. 25, 2008, the disclosure of each of which is hereby incorporated in its entirety by reference.

The present invention concerns oligonucleotide sequences that inhibit the expression of the chimera CYCLIN D1/TROP2 and their use in the medical field. In particular, the invention concerns RNA oligonucleotide sequences, or sequences that are transcribed into RNA or analogous molecules able to silence the expression of the CYCLIN D1/TROP2 chimeric mRNA and their use in the treatment and the prevention of tumors.

Post-transcriptional maturation of RNA has a fundamental role in the control of protein expression. One of the key events in this maturation is the process of splicing, i.e. the elimination of the introns (non-coding regions) and the fusion of the exons (coding regions and untranslated ends), in order to form a continuous molecule of messenger RNA (mRNA). About 70% of human genes normally undergo alternative splicing [1], i.e. variations in the choice of the exons that form the mature mRNA. This allows the production of different open reading frames (ORFs) from the same nucleotide sequence or the modulation of gene expression, if the alternative exons include the untranslated regulatory regions at the 5' and 3' ends of the RNA. Various types of sequences can be used in the splicing process: among the most common ones are the dinucleotides GT and AG at the beginning and at the end of the intronic sequences, which can therefore be recognized and removed by the splicing apparatus. Defects in this process, e.g. caused by mutations in the nucleotide regulatory sequences or in the splicing apparatus, are frequent and cause many inherited diseases [2, 3]. Splicing defects are often found also in human tumors, where they can have a causative role and be associated with a higher aggressiveness of the tumor disease [4, 5].

mRNA maturation can also take place through the splicing of two independent RNAs (trans-splicing), with the production of fusion (chimeric) RNAs without any recombination at the DNA level, this latter being a lesion which is frequently found in human tumors. In the protozoan trypanosoma all mRNAs carry a common leader sequence, which derives from a process of trans-splicing [6]. A similar process of RNA maturation has been described in several other species ([7], and references therein), including mammalian ones ([8], and references therein). Also in the trans-splicing process various sequences can be utilized to signal the junction borders [9-11].

It is known that the CYCLIN D1/TROP2 chimera plays an oncogenic role (37). The authors of the present invention have demonstrated and further expanded the knowledge relating to the existence of a chimeric mRNA deriving from the fusion between the transcripts for CYCLIN D1 and TROP2 (FIG. 1, A) in the tumor cell lines MCF7 and OVCA-432, by means of copy-DNA (cDNA) sequencing and RNAse protection experiments (FIG. 2). Cyclin D1 is a cell-cycle regulatory molecule that can stimulate tumor growth if overexpressed. Cyclin D1 overexpression is frequently found in human tumors, and it is generally caused by rearrangements at the DNA level. A second mechanism of Cyclin D1 overexpression is gene amplification, which is very frequent in human carcinomas, such as breast, head and neck, bladder, ovarian and esophageal cancers [12, 13], and cause an increase in the copy number of the CYCLIN D1 gene. A third mechanism is represented by inversions or deletions in the CYCLIN D1 gene, e.g. in parathyroid adenomas; this leads to the transcription of a short version of the corresponding mRNA, devoided of most of its 3' untranslated region, which is responsible for the induction of degradation of the mRNA itself [14]. This mRNA (SHORT CYCLIN) is therefore more stable than the full-length version and becomes an oncogene (a gene that causes cancer) [15-17]. It has to be noted that this occurs without changes/mutations in the corresponding Cyclin D1 protein.

Trop-2 (TACSTD2 gene) [18-21] is a trans-membrane glycoprotein that transduces a cytoplasmic calcium signal [22] and is involved in cell-cell and cell-substratum adhesion in epithelial tissues. Also Trop-2 is overexpressed in the majority of human cancers [19, 23], and is a potent stimulator of tumor growth. This stimulatory capacity depends on the presence of a protein kinase C (PKC) phosphorylation site at serine 303 in the cytoplasmic region of Trop-2 and on intact cytoplasmic signaling by PKC [24].

In the CYCLIN D1/TROP2 chimeric mRNA (chimera) that was isolated by the inventors, the short form of CYCLIN D1 is fused with the full-length transcript for TROP2. Both of these elements have normal sequences, without nucleotide mutations, and include the entire coding sequence. It has been confirmed experimentally, by means of cytofluorimetric analyses and Western blotting of cell lines that express the chimera, that the chimera is translated into two independent polypeptides corresponding to the normal Cyclin D1 and Trop-2 proteins (FIG. 3).

Since the CYCLIN D1 gene is frequently recombined in tumors, as described above, an investigation wa carried out on the presence of rearrangements at the DNA level that would bring together CYCLIN D1 and TROP2 on the same chromosome in a single transcriptional unit. Polymerase Chain Reaction (PCR), Southern blotting and Fluorescence In-Situ Hybridization (FISH) analyses performed on cell lines expressing the chimera showed the absence of translocations and recombinations at the gene level (FIG. 4). Therefore the CYCLIN D1/TROP2 chimera derives from a trans-splicing event that joins mRNA molecules independently originated from the corresponding genes. Since the sequences around the junction are different from those commonly used in trans-splicing, the mechanism of generation of the chimera is novel and important for the regulation of gene expression in particular in tumor cells.

Figure 5:
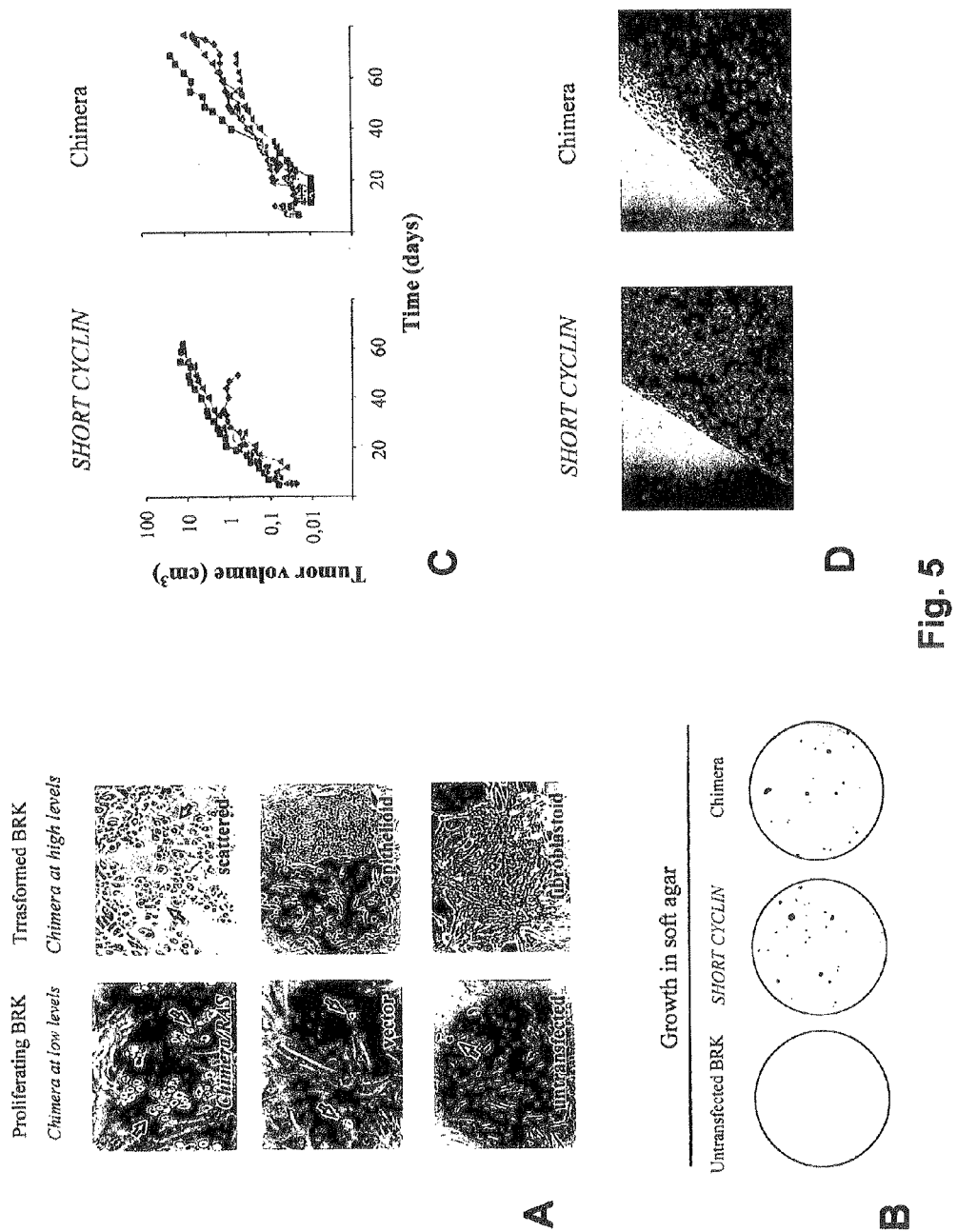
Figure 6:
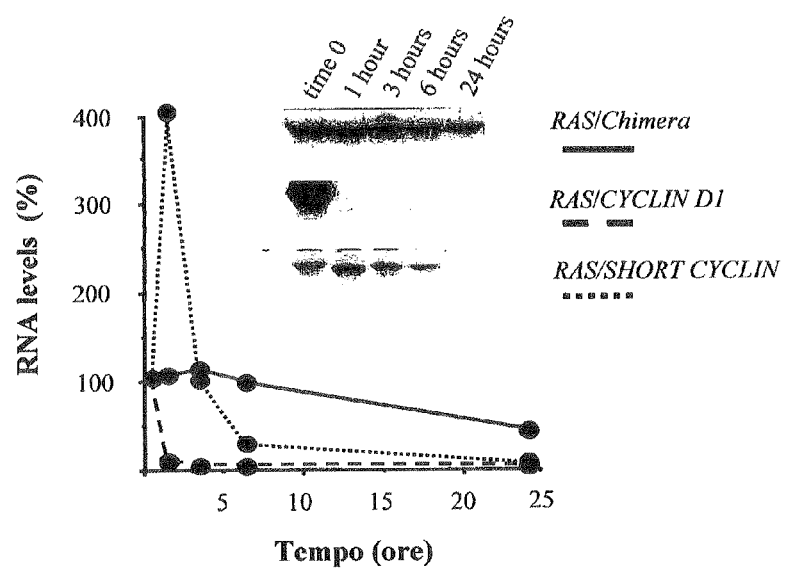

As far as the oncogenic potential of the CYCLIN D1/TROP2 chimera is concerned, since the CYCLIN D1/TROP2 chimera was isolated from cell lines derived from human tumors, and both Cyclin D1 and Trop-2 can induce cell proliferation, we investigated whether the chimera can stimulate cell growth (FIG. 5). To do this, we introduced the CYCLIN D1/TROP2 chimera together with a mutated RAS oncogene into BRK cells taken from newborn rats. Normally these cells have a limited life span in culture and die after a few months; the same behaviour was observed in BRK cells that expressed only the mutated RAS. On the contrary, when the CYCLIN D1/TROP2 chimera was added to the mutated RAS, the BRK cells became able to grow continuously, both on cell culture plates and without adhesion to a solid substratum (in soft agar), characteristics that are typically associated with tumor transformation [25-27]. Even more importantly, the BRK cells transformed by the CYCLIN D1/TROP2 chimera are able to grow as tumors in experimental animals (athymic nude mice). Therefore the CYCLIN D1/TROP2 chimera is not only able to stimulate growth, but behaves as an oncogene, transforming the cells that express it into tumor cells. This transforming ability depends on the greater stability of the chimeric mRNA, which is approximately 90 times that of the CYCLIN D1 mRNA (FIG. 6). Of interest, the chimeric mRNA is also much more stable than the SHORT CYCLIN previously described. Another cofactor of transformation is represented by the additional expression of Trop-2.

Figure 7:
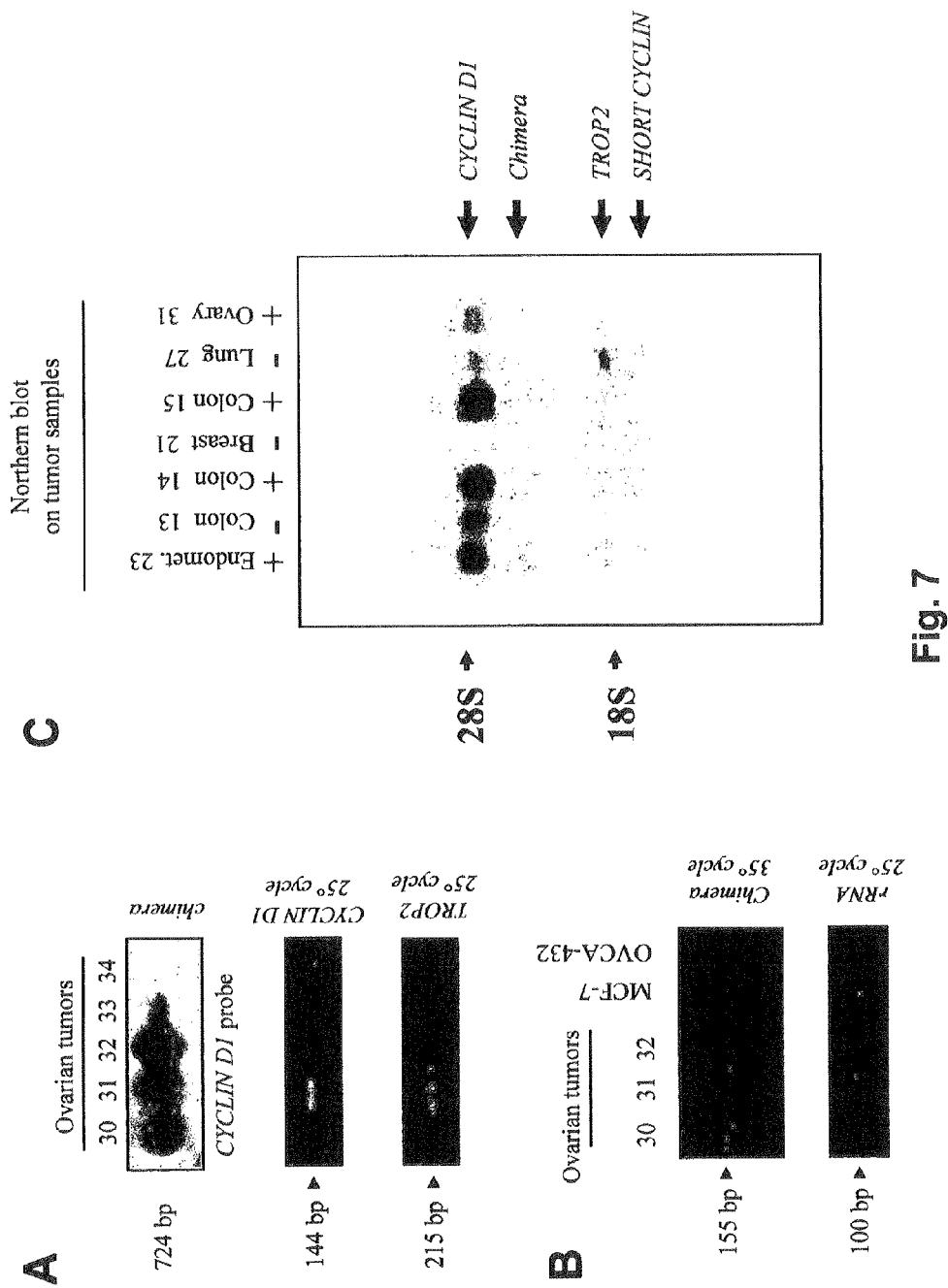
Figure 8:
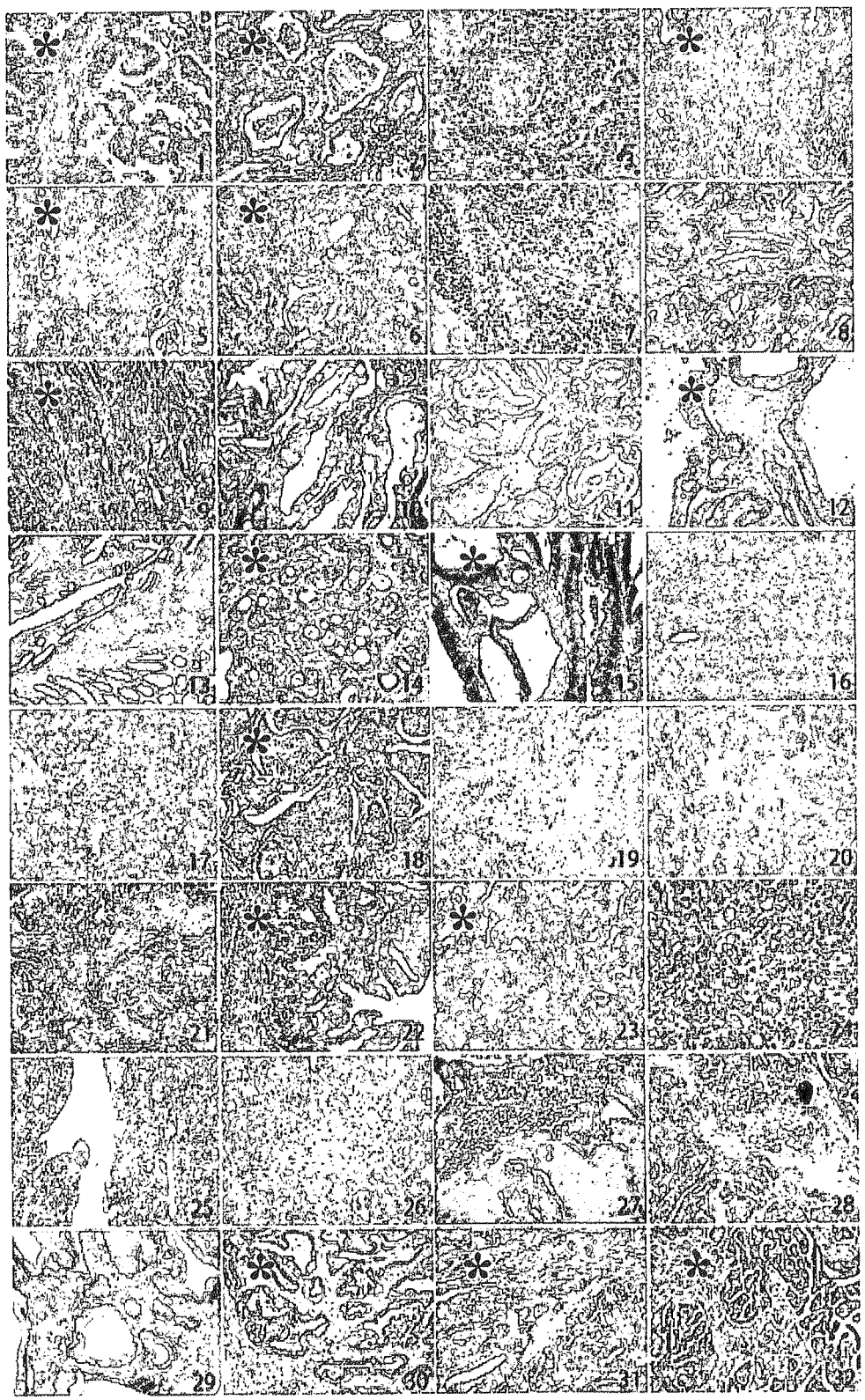

Since the CYCLIN D1/TROP2 chimera displays oncogenic potential, the authors of the present invention studied its expression in normal human tissues and several types of tumor. Forty tumors of various origin (stomach, colon, breast, endometrium, kidney, lung, ovary) were analyzed by Northern blot and/or PCR of the cDNA, with probes and oligonucleotide primers that were specific for the chimera (FIGS. 7 and 8). Our analyses have demonstrated that the CYCLIN D1/TROP2 chimera is frequently expressed in human tumors (Table 1 and 2).

Table 1 shows the levels of the TROP2 and CYCLIN D1 mRNAs and of their CYCLIN D1/TROP2 mRNA fusion in a series of human tumors.

TABLE 1

| 1 | Stomach | +/-- | + | + |
|---|---------|------|----|----|
| 2 | Stomach | +++  | +++ | ++ |
| 3 | Stomach | +++  | ++ | -  |
| 4 | Stomach | ++   | +/- | +  |
| 5 | Stomach | +++  | +/- | +  |
| 6 | Stomach | +    | +/- | +  |
| 7 | Stomach | +    | +/- | -  |
| 8 | Colon   | ++   | ++ | -  |
| 9 | Colon   | +++  | +/- | +  |
| 10 | Colon  | -    | +/- | -  |
| 11 | Colon  | +/-  | ++ | -  |
| 12 | Colon  | ++   | +/- | +  |
| 13 | Colon  | +/-  | ++ | -  |
| 14 | Colon  | ++   | ++ | +  |
| 15 | Colon  | ++   | ++ | +  |
| 16 | Breast | ++   | ++ | -  |
| 17 | Breast | ++   | +/-- | - |
| 18 | Breast | +    | +/- | ++ |
| 19 | Breast | ++   | +/- | -  |
| 20 | Breast | ++   | +/- | -  |
| 21 | Breast | ++   | +  | -  |
| 36 | Breast | ++   | +  | -  |
| 37 | Breast | +    | ++ | -  |
| 38 | Breast | +/-- | +/- | - |
| 39 | Breast | ++   | +++ | - |
| 40 | Breast | ++   | ++ | -  |
| 22 | Endometrium | +++ | + | + |
| 23 | Endometrium | +++ | + | + |
| 24 | Kidney | +    | +  | +  |
| 25 | Kidney | +/-- | ++ | -  |
| 26 | Kidney | +/-  | +/- | - |
| 27 | Lung   | ++++ | +/- | - |
| 28 | Ovary  | +/-- | ++ | -  |
| 29 | Ovary  | +    | +  | -  |
| 30 | Ovary  | +/-  | +  | +  |
| 31 | Ovary  | +++  | +++ | + |
| 32 | Ovary  | ++   | +  | +  |
| 33 | Ovary  | +    | +  | +/- |
| 34 | Ovary  | +    | +  | -  |
| 35 | Ovary  | +/-  | +  | +  |

Legend: N°: tumor numbers are as in Table 2 and FIGS. 6 and 7. The relative amounts of the TROP2, CYCLIN D1 and chimera mRNAs were validated by Northern blot and routinely quantified by PCR of the cDNA. +/-- and +/-: barely and clearly detectable, respectively, at the 30th amplification cycle; +, ++ and +++: barely detectable, clearly detectable and abundant, respectively, at the 25th amplification cycle. Tumors that express the CYCLIN D1/TROP2 chimera are highlighted in grey.

Table 2 shows the clinico-pathological characteristics of the tumors that were analysed for the expression of the CYCLIN D1/TROP2 chimera

TABLE 2

| N° | Organ | Diagnosis | Stage | Grade | DNA1 | DNA2 | % S1 | % S2 | p53 | Her-2 | CD34 | Ki-67 | Bcl-2 |
|---|---|---|---|---|---|---|---|---|---|---|---|---|---|
| 1 | Stomach | Adk intest. | T2N1 | G2 | 1.74 | | *** | | neg | ** | *** | * | neg |
| 2 | Stomach | Adk intest. | T2N0 | G2 | 1.88 | | ** | | * | neg | *** | * | neg |
| 3 | Stomach | Adk diffuse | T2N0 | | 1 | | ** | | * | * | *** | ** | neg |
| 4 | Stomach | Adk intest. | T1N0 | G2 | 1.44 | | ** | | * | neg | neg | * | neg |
| 5 | Stomach | Adk intest. | T2N1 | G2 | 1.28 | 1.65 | ne | *** | neg | ** | *** | ** | neg |
| 6 | Stomach | Adk intest. | T2N1 | G2 | 1.41 | | ** | | | | | | |
| 7 | Stomach | Adk diffuse | T2N1 | | 1 | | neg | | * | neg | ** | ** | neg |
| 8 | Sigma | Adk | T3N0 | G2 | 1 | | ** | | neg | neg | ** | ** | neg |
| 9 | Ileo-cecum | Adk | T4N0 | G3 | | | | | | | | | |
| 10 | Right colon | Adk | T4N1M1 | G2 | 1 | | ** | | ** | ** | ** | ** | * |
| 11 | Ileo-cecum | Adk | T3N0 | G2 | 1 | | ** | | ** | * | * | ** | * |
| 12 | Left colon | Adk | T3N0 | G2 | 1.07 | 1.69 | ** | | * | ** | * | ** | neg |
| 13 | Left colon | Adk | T2N0 | G2 | 1.9 | | *** | | *** | * | ** | *** | * |
| 14 | Left colon | Adk | T3N2 | G2 | 1.77 | | ** | | *** | * | * | ** | ** |
| 15 | Left colon | Adk | T2N0 | G2 | 1 | | ** | | neg | * | ** | ** | neg |
| 16 | Breast | Duct. Inf. K | T3N0 | G3 | .09 | | | | * | neg | ** | * | neg |
| 17 | Breast | Duct. Inf. K | T1N1 | G3 | 1.05 | | | | neg | ** | ** | ** | ** |
| 18 | Breast | Duct. Inf. K | T2N0 | G2 | 1 | | neg | | neg | * | * | * | *** |
| 19 | Breast | Duct. Inf. K | T2N0 | G3 | 1.61 | 1.77 | * | 7.4 | *** | * | ** | ** | * |
| 20 | Breast | Duct. Inf. K | T1N0 | G2 | | | | | neg | *** | ** | * | *** |
| 21 | Breast | Duct. Inf. K | T2N1 | G3 | 1.43 | 2.89 | ** | 37 | *** | *** | ** | ** | neg |
| 22 | Endometrium | Adk | 1C | G3 | 1 | | *** | | * | neg | ** | ** | neg |
| 23 | Endometrium | Adk | 1B | | 1 | | * | | | neg | ** | | *** |
| 24 | Kidney | K | T2N0 | G2 | 1.39 | 2.02 | *** | 22 | | | | | |
| 25 | Kidney | K clear cells | T1N0 | G2 | 1 | | neg | | neg | * | *** | * | ** |
| 26 | Kidney | K oncocytoma | | | 1.00 | | neg | | neg | *** | *** | neg | ** |

Legend: N°: tumor numbers are as in Table 1 and FIGS. 6 and 7. Adk: adenocarcinoma; K: carcinoma; Duct. Inf.: ductal infiltrating. DNA1: DNA index of the main cell population, where 1 indicates diploidy; DNA2: DNA index of the secondary cell population. % S: percentage of tumor cells in the S phase of the cell cycle, in the main (% S1) and in the secondary (% S2) cell populations; ne: not evaluable. p53: nuclear p53 expressing cells, Ki-67: mitotic cells, ER: estrogen receptor, PgR: progesterone receptor; neg: <5%; *: 5-33%, : 34-66%, * 67-100% of specific antibody labeling. CD-34: *: high, : medium, * low neo-vascular density, neg.: no detectable staining;. Tumor N° 10 presents with metastatic liver disease. Tumors expressing the CYCLIN D1-TROP2 mRNA chimera are highlighted in grey A striking example is that of the intestinal cell type gastric cancers, which express the CYCLIN D1/TROP2 chimera in all of the cases analyzed (5 out of 5). The expression of the chimera is not determined by the expression levels of the individual CYCLIN D1 and TROP2 mRNAs; various tumors express the chimera in the presence of hardly detectable amounts of the two mRNAs (for example gastric cancers), while other tumors do not express the chimera even in the presence of very high levels of both mRNAs (for example breast cancers). This suggests that the generation of the CYCLIN D1/TROP2 chimera is a regulated phenomenon.

A parallel analysis was performed on a series of normal human tissues, from colon, kidney, lung, pancreas, placenta, prostate, stomach, uterus and skin. None of the normal tissues that were analysed expresses the chimeric mRNA, with the sole exception of skin keratinocytes, which are characterized by a very high proliferation rate and Trop-2 expression levels.

The oncogenic potential of the CYCLIN D1-TROP2 chimera and its almost exclusive expression in tumors make the chimera an important diagnostic tool and therapeutic target for applications in oncology.

Since the chimera is an mRNA fusion, in the absence of DNA recombination between the genomic loci involved, the method of detection of the chimera must start from the cell/tissue RNA, which is much more unstable and prone to degradation than DNA. Archive tumor biopsies, that have been fixed in buffered formalin and embedded in paraffin, according to cancer pathology standard procedures, can be used for the extraction of nucleic acids. The quality of the nucleic acids extracted from these samples is variable, and influences further analyses.

Regarding the detection of specific transcripts, the classical methods used in the research laboratory, such as Northern blotting and RNAse protection, cannot be transferred easily to a medium/high throughput clinical setting characterized by stringent limitations in the amounts of material (human tissues) available. These methods in fact require large amounts of intact RNA (of the order of tens of micrograms) and accurate optimization, and use the radioisotope [$^{32}$P] to achieve the necessary sensitivity of detection.

In the cells/tissues that express the fusion mRNA, neither the DNA nor the individual mRNAs and proteins corresponding to Cyclin D1 and Trop-2 are in any way altered. Moreover both molecules are present and important in normal tissues. It is noteworthy also that the CYCLIN D1/TROP2 chimera performs its pro-oncogenic action already at low levels of expression.

Therefore, considering what has been detailed above, there is clearly the need to have a method to inhibit the expression of the CYCLIN D1/TROP2 chimera with high efficacy, that can virtually reduce the expression of the chimera to zero, and with high specificity towards the fusion RNA molecule, with minimal to no effects on the two individual CYCLIN D1 and TROP2 partners. Moreover, there is the need to provide a detection method to reveal the presence of the CYCLIN D1/TROP2 chimera that can be sensitive, robust, quantitative and potentially high-throughput.

The authors of the present invention have now set up an innovative system for the inhibition of the expression of the CYCLIN D1/TROP2 chimera that is effective and highly specific. To do this, according to the present invention, the mechanism of RNA silencing was exploited, designing a silencing RNA (siRNA) which include the sequence of the junction point of the chimera. An oligonucleotide containing the siRNA in a hairpin structure (siRNA-CH) was subcloned into appropriate vectors (plasmid and lentiviral vectors). In parallel an oligonucleotide (siRNA-MM) containing two mutated nucleotides with respect to the target sequence (one in region derived from the CYCLIN D1 and one in the region derived from TROP2) was also synthetized and subcloned; this siRNA-MM does not anneal completely to the target sequence and was used as a negative control. The sequences of the oligonucleotide pairs corresponding to each siRNA are shown in FIG. 1, C.

Figure 10:
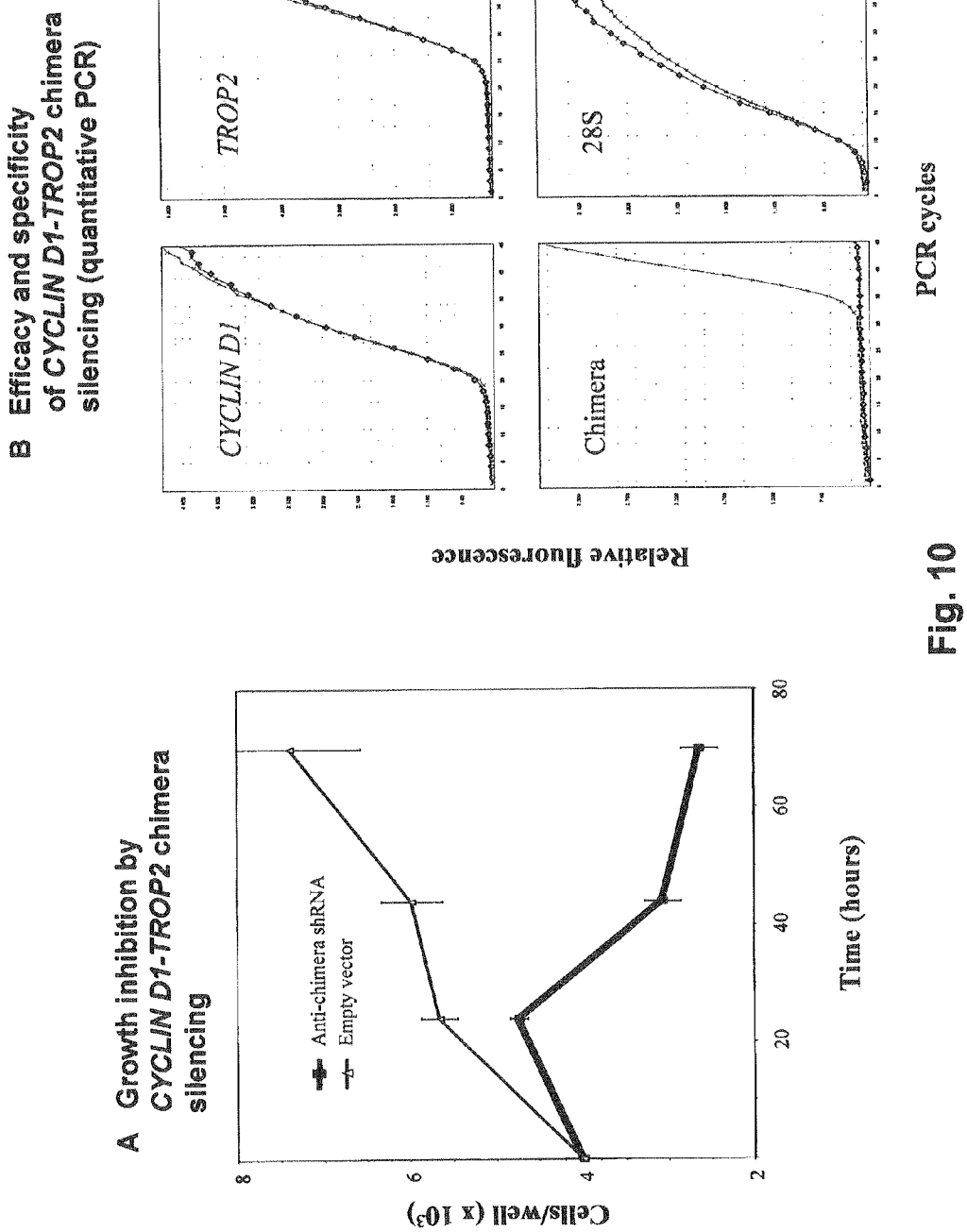

The vectors containing these siRNAs were transfected into cells that express the chimera. The levels of chimera in these cells were measured with the method that had been previously set up (real-time quantitative PCR of cDNA). In parallel, the levels of expression of the RNAs of the two partners, CYCLIN D1 and TROP2, and of the 28S rRNA used as a control, were also measured using a similar procedure. In these same cells the rate of growth was also monitored (FIG. 10). The silencing of the CYCLIN D1/TROP2 chimera was shown to be extremely efficient and specific. The expression of the chimera was reduced to zero by the specific siRNA, while the levels of CYCLIN D1 and TROP2 remained unchanged, equal to those of the original cells (and of the technical controls commonly used, in particular the cells transfected with an empty vector). Along with the inhibition of the expression of the CYCLIN D1/TROP2 chimera, cell growth was also strongly inhibited.

Moreover, the authors of the present invention have set up a method of analysis by means of quantitative PCR of the cDNA (RT-PCR) that can detect the expression of the CYCLIN D1/TROP2 chimera in cells and tissues. For this purpose a series of specific primers for DNA synthesis that can amplify the region around the junction point in the chimera were designed. The reaction conditions (enzyme, buffer, annealing temperature) for each pair of primers were optimized by means of PCR on cDNA prepared from total RNA extracted from cells expressing the chimera.

The PCR reactions were performed in a gradient thermocycler to test various annealing temperatures in parallel. To increase the sensitivity of the method reamplifications of PCR products with at least one primer internal to the fragment obtained in the first round were also performed. The end products of the PCR reactions were run on agarose gels and stained with ethidium bromide; single bands with the expected molecular weight were sequenced, and their sequences were compared with that expected for the amplification of the CYCLIN D1/TROP2 chimera. This allowed the selection of three primer pairs and related amplification conditions, with the possibility to use them in single or nested PCR reactions: PRAD1.F3 and T2.F5c (94° C., 1 min; 68° C., 1 min; 72° C., 1 min; 35 cycles); PRAD1.F4 and T2.F5tris (94° C., 1 min; 59° C., 1 min; 72° C., 1 min; 35 cycles); PRAD1.F5 and T2.F5tris (94° C., 1 min; 64° C., 1 min; 72° C., 1 min; 35 cycles). The sequences of these primers are shown in FIG. 1, B.

Figure 9:
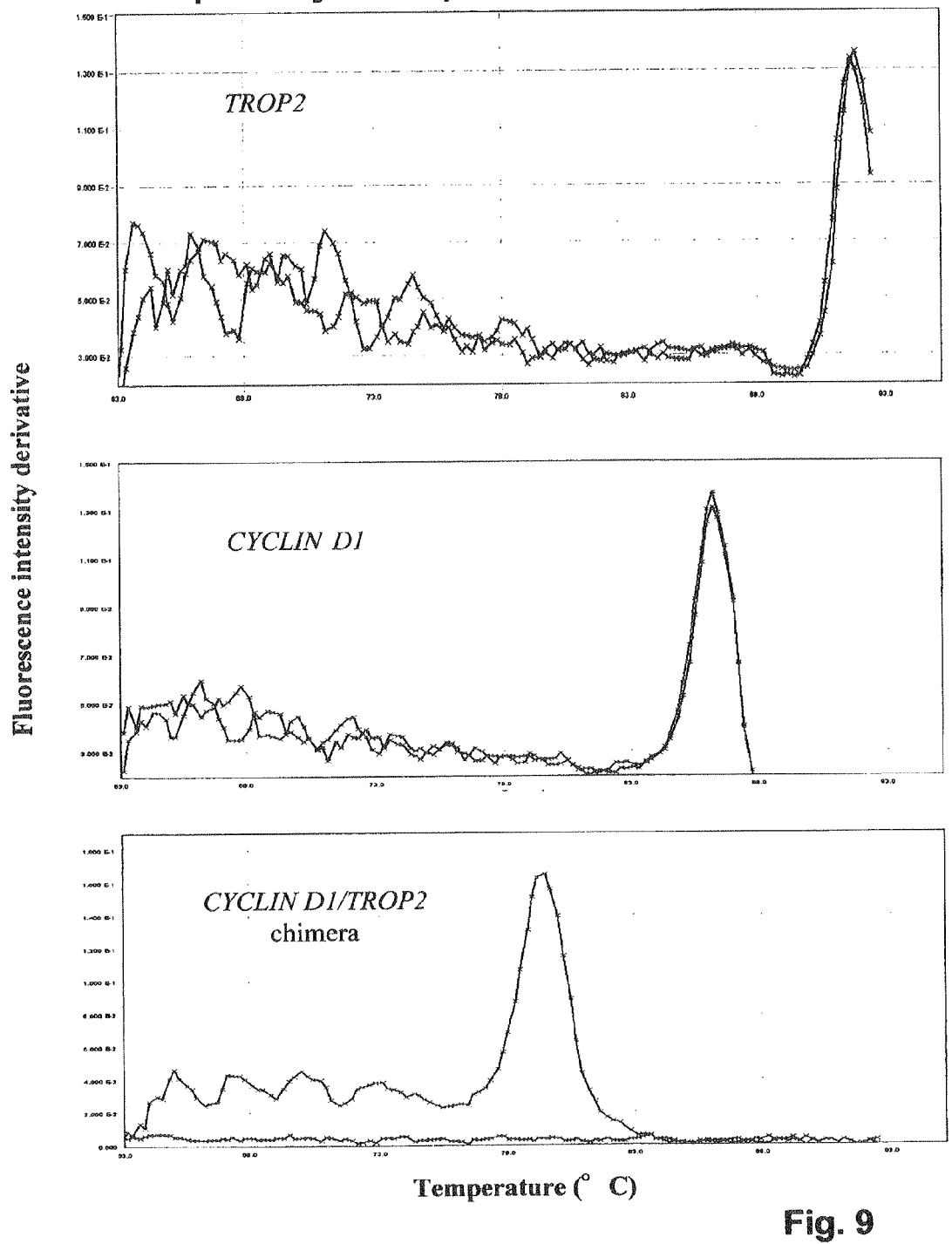

The primer pair PRAD1.F4/T2.F5tris, which is able to amplify the chimera in an efficient and specific way (presence of a single band), was subsequently tested in real-time quantitative PCR in the presence of Sybr Green, on cDNAs prepared from cells that express the chimera. The amplification cycle was the following: 94° C., 30 sec; 60° C., 30 sec; 72° C., 30 sec; 45 cycles. The fluorescence emission was measured during the reaction, and dissociation curves of the PCR products were run at the end of each reaction (FIG. 9). The presence of a single peak, at the temperature in which 50% of the PCR product is dissociated, confirmed the specificity of the reaction. Therefore the real-time quantitative PCR analysis has proven to be a method of analysis able to detect in a specific manner and to quantify the presence of the CYCLIN D1/TROP2 chimera in cells and tissues, starting from small amounts of material (1 μg total RNA). It was shown that a better alternative to formalin fixation in order to reveal the CYCLIN D1/TROP2 chimera is provided by the quick freezing of the tissue immediately after collection, followed by storage at low temperatures (−80° C.), a method that can already be used in dedicated collection centers. Moreover the procedure here described is easily transferrable to a medium-high throughput setting, for example using a robotic station for the processing of the samples and the assembly of the reactions. Robots for this purpose are already available on the market (es. TECAN, Switzerland).

An important result of the tests that were carried out to set up this diagnostic technique has been the validation of the primer sequences able to specifically amplify the junction region of the CYCLIN D1/TROP2 chimera.

Therefore specific embodiments of the present invention are an oligonucleotide sequence (siRNA), or analogous molecules, able to silence the expression of the CYCLIN D1/TROP2 chimeric mRNA, such siRNA being a ribonucleotide sequence complementary to the CYCLIN D1/TROP2 chimeric mRNA comprising or having the following CYCLIN D1/TROP2 junction sequence 5'GAGAGAGAGAGAAAGGAGCCC 3' (SEQ ID NO:21). Preferably, siRNA is a hairpin.

Moreover, another embodiment of the present invention is a vector comprising the sequences as defined above and a host cell comprising the said vector.

A further embodiment of the present invention is a pharmaceutical composition comprising or consisting in the sequences as defined above or comprising or consisting in the vector as defined above as the active ingredient, together with one or more adjuvants and/or excipients that are pharmaceutically acceptable.

Another embodiment of the present invention is the use of the sequences or the vector or the composition as defined above for the preparation of a medicament for the cure or the prevention of tumors such as, for example, stomach, colon, breast, endometrium, ovary, kidney and lung cancers.

A further embodiment of the present invention is represented by a kit for the in-vitro detection and quantification of the CYCLIN D1/TROP2 chimera in a biological sample comprising or consisting in the following PCR primers having the following sequence:

```
                                              (SEQ ID NO: 4)
(forward)      5' CTGGCCGCAATGACCCCGCA 3'

(SEQ ID NO: 9)
(reverse)      5' GGCGGAGGAACGCGGACCGG 3'

(SEQ ID NO: 5)
(forward)      5' GCGGGATCCAAGGGAAAGCTTCATTCT 3'
```

| (reverse) | 5' GAGGCGCGGGGACTCGTCGG 3' (SEQ ID NO: 10) |
| --- | --- |
| (forward) preferably, | 5' GCGGGATCCCCTTGTTGTTGGTTGTTT 3' (SEQ ID NO: 6) |
| (forward) | 5' GCGGGATCCAAGGGAAAGCTTCATTCT 3' (SEQ ID NO: 5) |
| (reverse) | 5' GAGGCGCGGGGACTCGTCGG 3' (SEQ ID NO: 10) |

Moreover another embodiment of the preset invention is a method for the in-vitro detection and quantification of the CYCLIN D1/TROP2 chimera in a biological sample using the following primers for real-time PCR:

| (forward) | 5' CTGGCCGCAATGACCCCGCA 3' (SEQ ID NO: 4) |
| --- | --- |
| (reverse) | 5' GGCGGAGGAACGCGGACCGG 3' (SEQ ID NO: 9) |
| (forward) | 5' GCGGGATCCAAGGGAAAGCTTCATTCT 3' (SEQ ID NO: 5) |
| (reverse) | 5' GAGGCGCGGGGACTCGTCGG 3' (SEQ ID NO: 10) |
| (forward) preferably, | 5' GCGGGATCCCCTTGTTGTTGGTTGTTT 3' (SEQ ID NO: 6) |
| (forward) | 5' GCGGGATCCAAGGGAAAGCTTCATTCT 3' (SEQ ID NO: 5) |
| (reverse) | 5' GAGGCGCGGGGACTCGTCGG 3' (SEQ ID NO: 10) |

The present invention will now be described by way of illustration and example, according, but not limited, to some of its preferred embodiments, with particular reference to the figures of the enclosed drawings.

FIG. 1. Main sequences forming the object of the invention.
(A) Sequence of the CYCLIN D1/TROP2 fusion. The vertical bar marks the junction point between CYCLIN D1 and TROP2. (B) Primers used to reveal the CYCLIN D1/TROP2 chimeric mRNA by means of quantitative PCR. (C) Sequences transcribed into the siRNA able to silence the expression of the CYCLIN D1-TROP2 chimeric mRNA, or ineffective siRNA, used as control (siRNA-MM).

FIG. 2. Expression of the CYCLIN D1-TROP2 chimeric mRNA in human cancer cell lines.
(A) RNase protection. The RNA extracted from the human cell lines MCF7 (from breast cancer) and OVCA-432 (from ovarian cancer), and from L cells (from murine fibrosarcoma—negative control), was hybridized to a [$^{32}$P]-labelled, antisense RNA probe corresponding to the junction of the CYCLIN D1/TROP2 chimera. The RNA was then digested with specific RNAses, that degrade only single stranded, non hybridized RNA, and run on a polyacrylamide gel. The bands correspond to mRNAs that are complementary to the probe, which form double-stranded hybrids and are therefore protected from RNase. The arrow indicates the band corresponding to the CYCLIN D1/TROP2 chimera; arrowheads indicate the bands corresponding to the TROP2 and CYCLIN D1 mRNAs. Digested probe: negative control, without DNA from cells.
(B) RT-PCR. The cDNA synthesized from the indicated cell lines was amplified with primers upstream and downstream of the junction point of the CYCLIN D1/TROP2 chimera. The PCR products were run on an agarose gel and analyzed by Southern blotting with two [$^{32}$P] labelled probes which were specific for CYCLIN D1 and for TROP2. Arrowheads indicate the bands corresponding to the CYCLIN D1/TROP2 chimera. L/TROP2: L cells transfected with human TROP2. Mix: RNA from the L cell transfected with human TROP2 mixed with RNA from the human cell line Ovcar-3, that expresses the CYCLIN D1 but not TROP2; the absence of band in this sample indicates that the mere simultaneous presence of the two transcripts, without cellular factors, is not sufficient for the production of the chimeric mRNA.

FIG. 3. Expression of Cyclin D1 and Trop-2 proteins from the CYCLIN D1-TROP2 chimeric mRNA.
(A) BRK cells transfected with the CYCLIN D1/TROP2 chimera were stained with a fluorescent anti-Trop-2 antibody and analyzed by flow cytometry. (B) Protein extracts from these transfectants were analyzed by Western blot with an anti-Cyclin D1 antibody. Control BRK cells, transfected with the SHORT CYCLIN or untransfected, were analyzed in parallel.

FIG. 4. Lack of recombination between CYCLIN D1 and TROP2 genes.
(A) mRNA structure. Restriction maps of the CYCLIN D1/TROP2 chimeric mRNA and of the corresponding regions of the CYCLIN D1 and TROP2 genes; vertical bar: junction point between CYCLIN D1 and TROP2 in the chimera; star: corresponding positions in the two wild-type genes. At the bottom of the cartoon the positions of the probes used for Southern blot analyses are indicated. (B) Genomic structure. Southern blot analysis of DNA extracted from OVCA-432 cells (OVCA) and normal human lymphocytes (Peripheral Blood Leukocytes, PBL), digested with Pst I or Hind III resctriction enzymes, hybridized with either CYCLIN D1 or TROP2 specific probes. Positions of the molecular weight markers are shown on the left. If the chimeric mRNA were originated from a DNA fusion, Southern analysis of OVCA-432 DNA should reveal bands with identical molecular weight with both CYCLIN D1 and TROP2 probes. (C) FISH analysis. Nuclei of OVCA-432 and MCF-7 cells and control PBL were hybridized with genomic CYCLIN D1 and TROP2 probes. Arrowheads indicate hybridization with CYCLIN D1, arrows indicate hybridization with TROP2. OVCA-432 cells possess three to four copies of CYCLIN D1 and two copies of TROP2 per cell. MCF-7 cells possess four copies of CYCLIN D1 and two copies of TROP2 per cell. In all the cases analyzed the hybridizations of the two genes do not overlap; if the chimeric mRNA were to come from a DNA fusion the signals from the two genes would instead overlap in the cells that express the chimera FIG. 5. Oncogenic potential of the CYCLIN D1/TROP2 chimera (A) BRK cells transfected with the CYCLIN D1/TROP2 chimera together with the mutated RAS oncogene. Low levels of expression of the chimera (left, top,) induce cell proliferation; control BRK cells that do not express the chimera (vector and untransfected) are quiescent. Arrows indicate clusters of proliferating (left, top) or single quiescent cells with a rounded, refractile morphology. Higher expression levels of the chimera (right) make the BRK cells able to grow continuously in culture; three different morphologies of actively growing BRK cells are shown: scattered, epithelioid and fibroblastoid cells. Images are phase-contrast microphotographies, taken with a 40× objective. (B) Soft agarose colonies formed by the growth of BRK cells that have been transfected with the SHORT CYCLIN or with the CYCLIN D1/TROP2 chimera, together with mutated RAS.

Non-transfected BRK cells were used as negative control. (C) Growth curves of tumors generated in athymic nude mice by BRK cells transfected with the SHORT CYCLIN or with the CYCLIN D1/TROP2 chimera, together with mutated RAS; each curve corresponds to one tumor. (D) When subjected to histopathological analysis these tumors were found to have high cellular densities with polymorphic fibrosarcomatous appearance and palisades of fusiform cells, with the presence of a pseudo-capsule.

FIG. 6. Stability of the CYCLIN D1/TROP2 chimeric mRNA. BRK cells transfected with the CYCLIN D1/TROP2 chimera, the CYCLIN D1 or the SHORT CYCLIN, together with mutated RAS, were treated at time 0 with actinomycin D (an inhibitor of RNA neosynthesis). The corresponding mRNAs were extracted and quantified by Northern blot with a radioactive CYCLIN D1 probe (inset) at different times from the beginning of the treatment; the values were normalized (quantity at time 0 equal to 100%) and plotted. This allowed to calculate the half-life ($t_{1/2}$) of each mRNA, i.e. the time it takes for the amount of mRNA present in the cell to decrease by 50% in the absence of neosynthesis, which is a direct measurement of the mRNA stability. The CYCLIN D1/TROP2 chimeric mRNA half-life was 23 hours, while the CYCLIN D1 half-life was 15 minutes and the SHORT CYCLIN half-life was 5 hours.

FIG. 7. Expression of the CYCLIN D1/TROP2 chimeric mRNA by human tumors.
(A) Ovarian tumors. (top) Southern blot analysis of the PCR from the cDNA performed with specific primers for the chimera. (middle, bottom) Expression levels of CYCLIN D1 and TROP2 mRNAs determined by PCR (the 25° PCR amplification cycle is shown). (B) Expression of the CYCLIN D1/TROP2 chimera by tumors and cell lines, measured by PCR performed on cDNA. The PCR products at the 35° cycle were run on agarose gel and stained with ethidium bromide. The 28S rRNA was quantified in the same samples as a control. (C) CYCLIN D1/TROP2 chimera expression in human tumors, measured by Northern blot with a radioactive probe corresponding to the junction region. Low-stringency hybridization detects the chimeric mRNA as well as the mRNAs corresponding to the individual transcripts. The organ of origin for each tumor is indicated; numbers are as in Table 1. Endomet.: endometrium. The symbols + and − indicate the presence or absence of the chimeric mRNA.

FIG. 8. Histopathology of the human tumors analysed for the expression of the CYCLIN D1/TROP2 chimera.
Panels 1-7: Gastric adenocarcinomas (1, 2, 4-6: intestinal type; 3, 7: diffuse); panels 1 and 2: moderately differentiated with inflammatory infiltrate; 3: perineural neoplastic infiltration.
Panels 8-15: Colorectal adenocarcinomas; 8, 10-13: moderately differentiated adenocarcinomas; normal intestinal crypts with inflammatory infiltrates (13, bottom); 9: poorly differentiated adenocarcinoma.
Panels 16-21: Ductal infiltrating breast carcinomas; 18, 21: moderately differentiated adenocarcinomas; 16, 17, 19: poorly differentiated forms; 20: more differentiated form with tubular formation.
Panels 22-23: Endometrial adenocarcinomas; 22: poorly differentiated tumor with necrotic areas.
Panels 24-26: Kidney carcinomas; 24, 26: renal oncocytomas with isomorphic tumor cells; 25: clear cell renal carcinoma.
Panel 27: Well differentiated squamous cell lung carcinoma (bottom) with normal overlying mucociliated mucosa (top).
Panels 28-32: Ovarian carcinomas; 28, 31, 32: serous cystoadenocarcinomas with marked stromal component; a psammoma is visible in 28 (upper right); 31 is poorly differentiated, 32 is moderately differentiated; 29: well-differentiated mucinous carcinoma; 30: endometrioid-type.
The tumors that express the CYCLIN D1/TROP2 chimera are indicated with a*. Pictures were taken with a 40× objective, except for panels 4, 5, 13, 25, 29, 30, that were taken with a 20× objective.

FIG. 9. Specificity analysis of the quantitative PCR reactions.
The amplification products that were obtained for the CYCLIN D1/TROP2 chimera, TROP2 and CYCLIN D1 by PCR reactions in the presence of Sybr Green were analysed for their dissociation profiles. The decrease of fluorescence with increasing temperatures was recorded (the graph shows the derivative of this decrease on the y axis, as normally visualized for this type of analysis). The presence of a single peak at a characteristic temperature for each reaction indicate the presence of a single and specific PCR product.

FIG. 10. Inhibition of the growth of cancer cells by RNA silencing of the CYCLIN D1/TROP2 chimeric mRNA.
(A) Growth curve of MCF7 tumor cells transfected with a vector expressing the specific siRNA for the silencing of the chimera (thick line). The growth of control MCF7 (transfected with the empty vector) was measured at the same time (thin line). Bars correspond to the standard error of the mean of cell numbers for each point. (B) mRNA levels of CYCLIN D1, TROP2 and CYCLIN D1/TROP2 chimera in the MCF7 cells tranfected with the siRNA targeted against the chimera, as measured by real-time quantitative PCR in the presence of Sybr Green, a dye that become fluorescent upon binding to the double-stranded DNA produced by the PCR reaction. The graph shows the intensity of emitted fluorescence for increasing cycles of the PCR amplification of the cDNA prepared from the transfectants with the siRNA against the chimera (♦) or with the empty vector (x). 28S ribosomal RNA levels were used as an internal quantification standard.

EXAMPLE 1

Study aiming at setting-up the oligonucleotide sequences able to inhibit the expression of the CYCLIN D1/TROP2 chimera and the methods for the detection of the expression of the CYCLIN D1/TROP2 chimera.

Materials and Methods

Cell Cultures.

The OVCA-432, Ovcar-3, and MCF-7 cell lines were grown in RPMI 1640 medium (GibcoBRL, Paisley, Scotland). The L cell line was maintained in DMEM. Media were supplemented with 10% fetal calf serum (GibcoBRL, Paisley, Scotland). BRK cells were prepared from kidneys of 8-day-old Sprague-Dawley rats as described [16]. Normal lymphocytes (Peripheral Blood Leukocytes, PBL) were obtained by centrifugation of heparinized blood over a density gradient (Ficoll-Hypaque). Keratinocytes were obtained from skin biopsies (two cases) immediately after surgery, upon treatment with collagenase type IV.

Transfections.

Transfections were performed as described in [32] or by lipofection (Gibco-BRL, USA).

Measurement of the Growth of Cells in Culture.

MCF-7 cells transfected with the siRNA specific for the CYCLIN D1/TROP2 chimera or with the empty vector as a control were seeded at a concentration of $4 \times 10^3$ cells/well in 96 wells (six replicate wells for each experimental point). Cell numbers for each time point were quantified by staining with crystal violet, as described [33].

Growth in Soft Agarose.

Growth of transformed BRK cells in soft agarose was measured as described previously [34]. Briefly, $3\times10^4$, $7\times10^4$ or $10^5$ BRK transfectants or primary BRK cells were seeded in each 3.5 cm-diameter dish. Visible colonies, originated by growing cells, were scored weekly after staining with methylene blue.

In Vivo Models: Xenografts in Athymic Nude Mice.

BRK cells transformed by the CYCLIN D1/TROP2 chimera or by the SHORT CYCLIN (plus the mutated RAS) were injected subcutaneously in 8-week old C57/B16 nude mice (10 mice per group). In all the groups tumor growth was measured weekly essentially as indicated [35].

Procedures involving animals and their care were conducted in conformity with institutional guidelines, in compliance with national (D.L. No. 116, G.U., Suppl. 40, Feb. 18, 1992; circolare No. 8, G.U., July, 1994) and international (EEC Council Directive 86/609, OJ L 358. 1, Dec. 12, 1987; Guide for the Care and Use of Laboratory Animals, United States National Research Council, 1996) laws and policies.

Statistical Analyses.

The statistical significance of the differences between the numbers of foci in different experimental groups in the in-vitro transformation assays was assessed by $\chi^2$ and Student's t tests. The statistical significance of the differences between different percentages of expression of the chimera by different tumor histotypes was assessed by Fisher exact tests.

Plasmids.

The pBJI-neo vector was provided by Dr. M. Davis (Stanford University, CA). The pUHD tet-off expression vector [36] was supplied by Dr. H. Bujard. The pPL-8 and pD1-1 plasmids containing the CYCLIN D1 and the Rc/CMV vector [16] were provided by Dr. P. Hinds (Harvard University, MA).

A full-length CYCLIN D1-TROP2 hybrid message was constructed by assembling the Eco RI/Hind III segment from pPL-8 and the Hind III/Xba I segment containing the chimera cDNA in the CDM8 vector [37]. A full length CYCLIN D1 cDNA was assembled by inserting the entire 3' UT of the CYCLIN D1 gene from pD1-1 (Hind III/Hind III segment) in the pPL-8 containing the SHORT CYCLIN cDNA.

Mutated or wild-type Ha-RAS genes were utilized as full-length genomic constructs, driven by their endogenous promoter (pUC-EJ and pUC-EC) [16].

The TROP2, CYCLIN D1 full length, SHORT CYCLIN and CYCLIN D1-TROP2 chimera were all expressed in pBJI-neo (expression driven by the HTLV-1 promoter) [38], pRC (CMV promoter) [16], pUHD (tetO-CMV chimeric promoter) [36] or pEYFP (CMV promoter) (Clontech, Palo Alto, Calif.).

DNA Sequencing.

DNA sequencing was performed with the Sanger method [39]. DNA sequences were analysed using the Genetics Computer Group program package [40].

Southern and Northern Blot Analyses.

Nucleic acids (DNA and RNA) were extracted and analysed as described [39]. Restriction enzymes were purchased from New England Biolabs (Beverly, Mass.). The filters on which the nucleic acids had been transferred were hybridized at high stringency with TROP2 or CYCLIN D1 cDNA radioactive probes, labelled as described [41].

A 307 by probe spanning the junction between CYCLIN D1 and TROP2 was utilized to reveal the chimera in tumors. This probe contains 123 bases of CYCLIN D1 and 183 bases at the 5' end of TROP2 [18] and was obtained by PCR amplification of the chimera with the primers PRAD1.F4/T2.F5bis. The probe was labelled with radioactive [$^{32}$P] using the procedure described in [41] modified by replacing the random primers with the specific primers used to generate the probe itself. Filters were hybridized at 58-62° C. in 0.5 M $Na_2PO_4$ 7% SDS and washed in 50 mM $Na_2PO_4$ 1% SDS at room temperature. The higher annealing temperature and one wash of one hour were utilized to reveal only the chimeric message; the lower annealing temperature revealed also the TROP2 and CYCLIN D1 mRNAs (FIG. 7C).

Western Blot Analyses.

Western blot analyses were performed as described [19]. Briefly, cell lysates were analysed by denaturing polyacrylamide gel electrophoresis (SDS-PAGE) and transferred to nitrocellulose filters. The filters were incubated with anti-human Trop-2 or anti-Cyclin D1 polyclonal antibodies for 1 h at room temperature. Antibody binding was revealed by chemiluminescence (ECL; Amersham, Aylesbury, UK) using an anti-rabbit secondary antibody conjugated to peroxidase (Calbiochem, La Jolla, Calif.).

PCR Analyses.

RNA was extracted from cells in culture with Trizol (Invitrogen), or as described in [42] from tissues that had been frozen immediately after collecting and subsequently pulverized in liquid nitrogen. Total or poly-$A^+$ RNA was reverse transcribed into the corresponding cDNA according to standard protocols (Pharmacia) and analysed by PCR (9700 PCR thermocycler, Perkin-Elmer, Foster City, Calif.; Mastercycler—Gradient, Eppendorf, Hamburg, Germany) [39]. The two primers for the PCR reactions were chosen from each of the following groups: forward (complementary to CYCLIN D1):

```
forward (complementary to CYCLIN D1):
                                      (SEQ ID NO: 3)
PRAD1.F2,      CCCAGCTGCCCAGGAAGAGC (SEQ ID NO: 4)
PRAD1.F3,      CTGGCCGCAATGACCCCGCA;

(SEQ ID NO: 5)
PRAD1.F4,      GCGGGATCCAAGGGAAAGCTTCATTCT;

(SEQ ID NO: 6)
PRAD1.F5,      GCGGGATCCCCTTGTTGTTGGTTGTTT.

Reverse: (complementary to TROP2):
                                      (SEQ ID NO: 7)
T2.F4bis,      ATCGTTGTCCACGAGCGCGT;

(SEQ ID NO: 8)
T2.F5bis,      TTGGTGGGACACGTGCAGTT;

(SEQ ID NO: 9)
T2.F5c,        GGCGGAGGAACGCGGACCGG;

(SEQ ID NO: 10)
T2.F5tris,     GAGGCGCGGGGACTCGTCGG.
```

PCR reactions were performed using various primer pairs spaced every 200 by on the chimera and revealed that both the 5' region of TROP2 and the region across the CYCLIN D1-TROP2 junction are difficult to amplify, irrespective of the primer pair used, probably because of the presence in this region of stable secondary structures. In fact the amplification efficiency improved using high annealing temperatures (68-72° C.), and specific reagents, such as 10% dimethysulfoxide in the reaction buffer together with "Perfect Match" (Stratagene, Calif.), and Amplitaq Gold (Applied Biosystems, California), or the buffers H or I from the "Failsafe" kit, (Epicentre, Madison, Wis.), with the Taq polimerase included in the same kit. The best results were obtained with these latter reagents, which were then used for all the subsequent PCR amplifications.

PCR amplification with the primer pair PRAD1.F4/T2.F5tris (94° C., 1 min; 59° C., 1 min; 72° C., 1 min; 35 cycles) efficiently revealed the presence of the chimeric mRNA in tumors. On the contrary, amplification of the chimera from cell lines required two consecutive PCR reactions: a first amplification using the primer pair PRAD1.F3/T2.F5c (94° C., 1 min; 68° C., 1 min; 72° C., 1 min; 35 cycles), followed by the reamplification of the PCR product with the primer pair PRAD1.F4/T2.F5tris and the cycling conditions described above.

The CYCLIN D1 mRNA was revealed with the primers SUF (forward, 5' ACAAACAGATCATCCGCAAACAC 3' (SEQ ID NO:11)) and SUR (reverse, 5' TGTTGGGGCTCCTCAGGTTC 3' (SEQ ID NO:12)) as described [43]. TROP2 mRNA was revealed with the primer pair T2.R3quad (forward, GCAGGACAACTGCACGTGTC (SEQ ID NO:13)) and T2.F4bis (reverse, ATCGTTGTCCACGAGCGCGT (SEQ ID NO:7)). PCR reactions were stopped after 20, 25, 30 and 35 cycles, and their products were analysed on ethidium bromide-agarose gels. Ribosomal 28S rRNA was amplified at the same time as internal control, with the primers 28SF (forward, 5' TTGAAAATCCGGGGGAGAG 3' (SEQ ID NO:14)) and 28SR (reverse, 5' ACATTGTTCCAACATGCCAG 3' (SEQ ID NO:15)) [44].

Genomic DNA from OVCA-432 and MCF-7 cells was analysed by PCR with two primer pairs across the junction point of the chimera to detect a possible recombination between the CYCLIN D1 and TROP2 loci. The primers used were the following: T2.R2t, forward, GACTGCCTCCGGGCCTGCCA (SEQ ID NO:16); T2.R2IV, forward, TCCTTTGCTCTTTCCCCCTT (SEQ ID NO:17); T2.F5c and T2.F5tris as reverse.

The amplification of the CYCLIN D1-TROP2 chimera was reproducibly obtained from 7 independent OVCA-432 cDNA in over 100 different experiments, and from 3 independent MCF-7 cDNA in over 40 experiments. All the PCR products had the expected sequence. Control L cells or reconstitution experiments where CYCLIN D1 RNA was mixed with TROP2 RNA in the reaction tube, before cDNA synthesis, never produced the chimera. This, together with the RNAse protection and Northern blot analyses, demonstrate that the chimera does not derive from experimental artifacts.

Quantitative PCR.

Total RNA from the cell lines indicated was extracted in Trizol (Invitrogen) following the indications of the manufacturer. RNA from 9 normal human tissues (each pooled from at least two individuals) was purchased from BD Biosciences-Clontech (Palo Alto, Calif.) and subjected to DNAse I (Ambion) treatment before cDNA synthesis by retrotranscription (RT). One µg of total RNA was used for each RT reaction, performed with the ImProm-II Reverse Transcriptase enzyme (Promega) according to standard protocols. Actual cDNA amounts obtained in each reaction were quantified by fluorescence emission after addition of ethidium bromide in solution [45]. Quantitative real time PCR reactions were performed using an ABI-PRISM 7900HT Sequence Detection System (PE Applied Biosystems, Foster City, Calif., USA) in the presence of the fluorescent dye SYBR-green (Power Sybr Green PCR Master Mix, Applied Biosystems), according to the manufacturer instructions. The primers that were used had been optimized for efficiency and specificity in previous PCR reactions. For quantitative amplifications the concentration of each primer was optimized at 200 nM, in a final reaction volume of 30 µl. 28S rRNA was used as internal standard. The primers used were PRAD1.F4 and T2.F5tris for the chimera; T2.R3quad and T2.F4bis for TROP2; SUF and SUR [43] for CYCLIN D1; 28SF and 28SR [44] for 28S rRNA. At the end of each amplification the dissociation curves of the amplification products were checked, to confirm the specificity of the amplification reaction.

RNAse Protection.

RNAse protection analyses were performed using poly-$A^+$ mRNA from OVCA-432, MCF-7 and L cells. A single-stranded RNA probe corresponding to the Hind III-Not I segment of the CYCLIN D1/TROP2 cDNA was transcribed in vitro in the presence of $[^{32}P]$-UTP (Promega Corporation, Madison, Wis.). The radioactive probe thus obtained was annealed to 20 µg of poly-A mRNA of each cell line at 55° C. overnight. RNA was then digested with RNAse A and T1 following the manufacturer's instructions (Ambion Inc., Austin, Tex.) and electrophoresed through 5% polyacrylamide gels.

FISH Analyses.

OVCA-432 and MCF-7 cells and control normal lymphocytes were analysed by two-color FISH analysis [21] using 15 kb-long genomic probes that were specific for TROP2 and CYCLIN D1. Both probes were labeled [39] using either digoxigenin-dUTP for TROP2 or biotin-dUTP for CYCLIN D1. Labeled probes were mixed with sheared human DNA, and hybridized to the nuclei of the tumor cell lines under study. Hybridization of TROP2 was revealed with anti-digoxigenin antibodies that were conjugated to a green fluorophore, hybridization of CYCLIN D1 was revealed with avidin that was conjugated to a red fluorophore.

RNA Silencing.

Silencing of the chimeric mRNA was performed utilizing sequences transcribed into silencing RNAs (siRNAs) [46], that were specific for the junction point of the CYCLIN D1/TROP2 chimeric mRNA, cloned into the pSUPER vector as described [28]. The plasmids with the silencing sequences and their controls were transfected into MCF7 cells following this procedure: cells were seeded in 96 well plates at 4000 cells per well, with 6 replicate wells for each measurement; 4 hours after seeding cells were transfected with 250 ng DNA and 0.25 µl Lipofectamine 2000 (Invitrogen) per well in 100 µl DMEM, according to the manufacturer instructions; the first measurement of cell number was performed 8 hours after transfection, and subsequently at the indicated times.

Immunofluorescence Analyses.

Cells were stained with the anti-Trop-2 antibodies 162-46.2 and T16 as described [18]. Anti-human Cyclin D1 polyclonal antibodies were supplied by Santa Cruz Biotechnology Inc. (Santa Cruz, Calif.). Fluorescence analyses were performed by flow cytometry (Vantage, Becton Dickinson, Sunnyvale, Calif.).

Histopathological and Immunohistochemical Analyses of Tumors.

Specimens of human cancers were snap frozen in liquid nitrogen immediately after surgery and stored at −80° C. Tumors were characterized for staging, grading, fraction of proliferating cells (KI-67), ploidy, neovascularization (CD34) and expression of p53, Her-2, Bcl-2 [47]. Tumor stages were classified according to the TNM or FIGO systems [47], where T indicates the tumor diameter (increasing from T1 to T4), N indicates lymphnode invasion (from N0 to N2) and M indicates metastatic diffusion to distant sites (M0 or M1). Immunohistochemical analysis of normal and neoplastic tissues was performed as described [[47], on sections with a five-micron thickness. Endogenous peroxidase activity was blocked by incubation with 3% $H_2O_2$ for 5 minutes. Sections were then incubated for 30 minutes with the appropriate biotinylated antibody, and the binding to the antibody was revealed by means of avidin-peroxidase and diamminobenzidine as chromogen (DAKO, Glostrup, Denmark): avidin binds to biotin, peroxidase reacts with diamminobenzidine forming a coloured compound.

REFERENCES

1. Johnson, J. M., et al., *Genome-wide survey of human alternative pre-mRNA splicing with exon junction microarrays.* Science, 2003. 302(5653): p. 2141-4.
2. Stenson, P. D., et al., *Human Gene Mutation Database (HGMD): 2003 update.* Hum Mutat, 2003. 21(6): p. 577-81.
3. Buratti, E., M. Baralle, and F. E. Baralle, *Defective splicing, disease and therapy: searching for master checkpoints in exon definition.* Nucleic Acids Res, 2006. 34(12): p. 3494-510.
4. Kalnina, Z., et al., *Alterations of pre-mRNA splicing in cancer.* Genes Chromosomes Cancer, 2005. 42(4): p. 342-57.
5. Pajares, M. J., et al., *Alternative splicing: an emerging topic in molecular and clinical oncology.* Lancet Oncol, 2007. 8(4): p. 349-57.
6. Murphy, W. J., K. P. Watkins, and N. Agabian, *Identification of a novel Y branch structure as an intermediate in trypanosome mRNA processing: evidence for trans splicing.* Cell, 1986. 47(4): p. 517-25.
7. Zhang, H., et al., *Spliced leader RNA trans-splicing in dinoflagellates.* Proc Natl Acad Sci USA, 2007. 104(11): p. 4618-23.
8. Horiuchi, T. and T. Aigaki, *Alternative trans-splicing: a novel mode of pre-mRNA processing.* Biol Cell, 2006. 98(2): p. 135-40.
9. Vellard, M., et al., *C-myb proto-oncogene: evidence for intermolecular recombination of coding sequences.* Oncogene, 1991. 6(4): p. 505-14.
10. Zhang, C., et al., *A candidate chimeric mammalian mRNA transcript is derived from distinct chromosomes and is associated with nonconsensus splice junction motifs.* DNA Cell Biol, 2003. 22(5): p. 303-15.
11. Ng, P., et al., *Gene identification signature (GIS) analysis for transcriptome characterization and genome annotation.* Nat Methods, 2005. 2(2): p. 105-11.
12. Bringuier, P. P., et al., *Expression of cyclin D1 and EMS1 in bladder tumors; relationship with chromosome 11q13 amplification.* Oncogene, 1996. 12: p. 1747-1753.
13. Jiang, W., et al., *Amplification and expression of the human cyclin D gene in esophageal cancer.* Cancer Res., 1992. 52: p. 2980-2983.
14. Motokura, T., et al., *A novel cyclin encoded by a bcl1-linked candidate oncogene.* Nature, 1991. 350: p. 512-515.
15. Hosokawa, Y., et al., *A small deletion in the 3'-untranslated region of the cyclin D1/PRAD1/bcl-1 oncogene in a patient with chronic lymphocytic leukemia.* Int. J. Cancer, 1998. 76: p. 791-796.
16. Hinds, P. W., et al., *Function of a human cyclin gene as an oncogene.* Proc. Natl. Acad. Sci. USA, 1994. 91: p. 709-713.
17. Lebwohl, D. E., et al., *A truncated cyclin D1 gene encodes a stable mRNA in a human breast cancer cell line.* Oncogene, 1994. 9: p. 1925-1929.
18. Fornaro, M., et al., *Cloning of the gene encoding TROP-2, a cell-surface glycoprotein expressed by human carcinomas.* Int. J. Cancer, 1995. 62: p. 610-8.
19. El-Sewedy, T., M. Fornaro, and S. Alberti, *Cloning of the mouse Trop2 gene—Conservation of a PIP2-binding sequence in the cytoplasmic domain of Trop-2.* Int. J. Cancer, 1998. 75: p. 324-331.
20. Linnenbach, A. J., et al., *Retroposition in a family of carcinoma-associated antigen genes.* Mol. Cell. Biol., 1993. 13: p. 1507-1515.
21. Calabrese, G., et al., *Assignment of TACSTD1 (alias TROP1, M4S1) to human chromosome 2p21 and refinement of mapping of TACSTD2 (alias TROP2, M1S1) to human chromosome 1p32 by in situ hybridization.* Cytogenet. Cell Genet., 2001. 92(1-2): p. 164-5.
22. Ripani, E., et al., *The human Trop-2 is a tumor-associated calcium signal transducer.* Int. J. Cancer, 1998. 76: p. 671-676.
23. Ohmachi, T., et al., *Clinical significance of TROP2 expression in colorectal cancer.* Clin Cancer Res, 2006. 12(10): p. 3057-63.
24. Basu, A., D. M. Goldenberg, and R. Stein, *The epithelial/carcinoma antigen EGP-1, recognized by monoclonal antibody RS7-3G11, is phosphorylated on serine* 303. Int. J. Cancer, 1995. 62: p. 472-479.
25. Land, H., L. F. Parada, and R. A. Weinberg, *Cellular oncogenes and multistep carcinogenesis.* Science, 1983. 222(4625): p. 771-8.
26. Shimizu, K., et al., *Three human transforming genes are related to the viral ras oncogenes.* Proc Natl Acad Sci USA, 1983. 80(8): p. 2112-6.
27. Wang, J., et al., *Identification of Trop-2 as an oncogene and an attractive therapeutic target in colon cancers.* Mol Cancer Ther, 2008. 7(2): p. 280-5.
28. Brummelkamp, T. R., R. Bernards, and R. Agami, *A System for Stable Expression of Short Interfering RNAs in Mammalian Cells.* Science, 2002. 296(5567): p. 550-553.
29. Moffat, J., et al., *A lentiviral RNAi library for human and mouse genes applied to an arrayed viral high-content screen.* Cell, 2006. 124(6): p. 1283-98.
30. Xi, S. and J. R. Grandis, *Gene therapy for the treatment of oral squamous cell carcinoma.* J Dent Res, 2003. 82(1): p. 11-6.
31. Arbuthnot, P. and L. J. Thompson, *Harnessing the RNA interference pathway to advance treatment and prevention of hepatocellular carcinoma.* World J Gastroenterol, 2008. 14(11): p. 1670-81.
32. Alberti, S., M. Nutini, and L. A. Herzenberg, *DNA methylation prevents the amplification of TROP1, a tumor associated cell surface antigen gene.* Proc. Natl. Acad. Sci. USA, 1994. 91: p. 5833-7.
33. Orsulic, S., et al., *Induction of ovarian cancer by defined multiple genetic changes in a mouse model system.* Cancer Cell, 2002. 1(1): p. 53-62.
34. Resnitzky, D., *Ectopic expression of cyclin D1 but not cyclin E induces anchorage-independent cell cycle progression.* Mol. Cell. Biol., 1997. 17: p. 5640-5647.
35. Garofalo, A., et al., *Comparative study on the metastatic behavior of human tumors in nude, beige/nude/xid and severe combined immunodeficient mice.* Invasion Metastasis, 1993. 13(2): p. 82-91.
36. Gossen, M. and H. Bujard, *Tight control of gene expression in mammalian cells by tetracycline-responsive promoters.* Proc Natl. Acad. Sci. USA, 1992. 89: p. 5547-5551.
37. Terrinoni, A., et al., *The Cyclin D1 gene contains a cryptic promoter that is functional in human cancer cells.* Genes Chromosomes Cancer, 2001. 31(3): p. 209-20.
38. Lin, A., et al., *Expression of T-cell antigen receptor heterodimers in a lipid-linked form.* Science, 1990. 249: p. 677-679.
39. Sambrook, J., E. F. Fritsch, and T. Maniatis, *Molecular cloning—A laboratory manual.* 2 ed. Molecular cloning—A laboratory manual, ed. J. Sambrook, E. F. Fritsch, and T. Maniatis. 1989, New York: Cold Spring Harbor Laboratory.
40. Devereux, J., P. Haeberli, and O. Smithies, *A comprehensive set of sequence analysis programs for the VAX.* Nucleic Acids Res., 1984. 12: p. 387-395.
41. Feinberg, A. P. and B. Vogelstein, *A technique for radiolabeling DNA restriction endonuclease fragments to high specific activity.* Anal Biochem, 1983. 132(1): p. 6-13.
42. Chomczynski, P. and N. Sacchi, *Single-step method of RNA isolation by acid guanidinium thiocyanate-phenol-chloroform extraction.* Anal Biochem, 1987. 162(1): p. 156-9.
43. Suzuki, R., et al., *Detection of cyclin D1 overexpression by real-time reverse-transcriptase-mediated quantitative polymerase chain reaction for the diagnosis of mantle cell lymphoma.* Am J Pathol, 2001. 159(2): p. 425-9.
44. Simpson, D. A., et al., *Retinal VEGF mRNA measured by SYBR green I fluorescence: A versatile approach to quantitative PCR.* Mol Vis, 2000. 6: p. 178-83.
45. Bonasera, V., S. Alberti, and S. A.c., *Protocol for high-sensitivity/long linear-range spectrofluorimetric DNA quantification using ethidium bromide.* BioTechniques, 2007. 43(2): p. 173-176.
46. Elbashir, S. M., et al., *Duplexes of 21-nucleotide RNAs mediate RNA interference in cultured mammalian cells.* Nature, 2001. 411(6836): p. 494-8.
47. Allred, D. C., et al., *Prognostic and predictive factors in breast cancer by immunohistochemical analysis.* Mod. Pathol., 1998. 11(2): p. 155-68.

The invention claimed is:

1. Oligonucleotide sequence (siRNA) able to silence the expression of the CYCLIN D1/TROP2 chimeric mRNA, said siRNA being characterized by the fact that it comprises a ribonucleotide sequence complementary to the CYCLIN D1/TROP2 chimeric mRNA junction sequence 5'GAGAGAGAGAGAAAGGAGCCC 3' (SEQ ID NO:21).

2. The oligonucleotide sequence according to claim 1, wherein the oligonucleotide sequence has a hairpin structure.

3. Vector comprising the oligonucleotide sequence as defined in claim 1.

4. Host cell comprising the vector as defined in claim 3.

5. Pharmaceutical composition comprising the oligonucleotide sequence as defined in claim 1 as the active ingredient, together with one or more adjuvants and/or excipients that are pharmaceutically acceptable.

6. A method of treating tumors, comprising administering to a patient in need thereof the oligonucleotide sequence as defined in claim 1.

7. The method according to claim 6, wherein the tumors are selected from the group consisting of stomach, colon, breast, endometrium, ovary, kidney and lung cancers.

8. Pharmaceutical composition comprising the vector as defined in claim 3 as the active ingredient, together with one or more adjuvants and/or excipients that are pharmaceutically acceptable.

9. A method for treating tumors, comprising administering to a patient in need thereof the vector as defined in claim 3.

10. A method for treating tumors, comprising administering to a patient in need thereof a therapeutically-effective amount of the composition as defined in claim 5.

11. The oligonucleotide sequence (siRNA) of claim 1, wherein the siRNA is selected from the group consisting of SEQ ID NO:1 and SEQ ID NO:2.

12. A method for treating tumors, comprising administering to a patient in need thereof a therapeutically-effective amount of the composition as defined in claim 8.

* * * * *